United States Patent [19]
Martinez et al.

[11] Patent Number: 4,952,580
[45] Date of Patent: Aug. 28, 1990

[54] PESTICIDAL POLYHALOALKENE DERIVATIVES

[75] Inventors: Anthony J. Martinez, Hamilton Square; Thomas G. Cullen, Milltown, both of N.J.

[73] Assignee: FMC Corporation, Philadelphia, Pa.

[21] Appl. No.: 270,903

[22] Filed: Nov. 9, 1988

Related U.S. Application Data

[63] Continuation-in-part of Ser. No. 161,575, Feb. 29, 1988, abandoned, which is a continuation of Ser. No. 870,055, Jun. 3, 1986, abandoned, which is a continuation-in-part of Ser. No. 747,142, Jun. 20, 1985, abandoned.

[51] Int. Cl.$^5$ ............... C07D 285/13; C07D 271/113; C07D 285/08; A61K 31/41
[52] U.S. Cl. ............... 514/236.2; 514/226.5; 514/361; 514/363; 514/364; 514/369; 514/423; 514/425; 514/443; 514/445; 514/448; 514/472; 514/514; 514/532; 514/549; 514/550; 544/49; 544/138; 546/277; 548/127; 548/129; 548/132; 548/136; 548/142; 548/144; 548/182; 548/194; 548/531; 548/545; 549/23; 549/62; 549/71; 549/481; 549/484; 558/17; 560/111; 560/153; 560/227
[58] Field of Search ............... 548/127, 129, 132, 136, 548/142, 144, 482, 194, 531, 552; 549/23, 62, 71, 481, 484; 558/17; 560/111, 153, 227; 544/49, 138; 546/277; 514/226.5, 236.2, 361, 363, 364, 369, 423, 425, 443, 445, 448, 472, 514, 532

[56] References Cited

U.S. PATENT DOCUMENTS

| | | | |
|---|---|---|---|
| 3,058,990 | 10/1962 | Harman | 71/90 |
| 3,080,405 | 3/1963 | Lursen | 568/843 |
| 3,463,856 | 8/1969 | Kado | 514/421 |
| 3,513,172 | 5/1970 | Brokke | 548/129 |

FOREIGN PATENT DOCUMENTS

| | | | |
|---|---|---|---|
| 138091 | 1/1985 | European Pat. Off. | 548/129 |
| 1528170 | 6/1968 | France | 548/129 |
| 49-8259 | 2/1974 | Japan | 548/129 |

*Primary Examiner*—Robert Gerstl
*Attorney, Agent, or Firm*—Stanford M. Back; Patrick C. Baker; H. Robinson Ertelt

[57] ABSTRACT

Polyhaloalkene compounds of the formula:

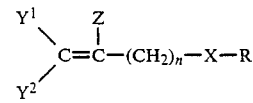

wherein X is sulfur, oxygen, or nitrogen, $Y^1$ and $Y^2$ are fluorine, Z is hydrogen or the same as $Y^1$ and $Y^2$, and n is 1–4; provided that:

(A) when X is sulfur, Z is fluorine and R is thienyl or substituted thienyl, thianaphthyl or substituted thianaphthyl, thiazolinyl or substituted thiazolinyl, oxadiazolyl or substituted oxadiazolyl, 3,4,4-trifluoro-3-butenyloxycarbonylmethyl, thiadiazolyl substituted by halogen or $R^2S$, wherein $R^2$ is 3,4,4-trifluoro-3-butenyl or $R^2$ is phenylmethyl or phenylthiomethyl each optionally substituted by halogen or nitro; or R is thiadiazolyl substituted by $R^3$, wherein $R^3$ is substituted aryl, arylalkyl, aryloxyalkyl, alkylthio, haloalkylthio, haloarylthio, cyanoalkylthio, arylalkylthio, aryloxyalkylthio, arylthioalkylthio, heterocycloalkylthio, alkenylthio, haloalkenylthio, halocycloalkylalkenylthio, wherein said aryl or heterocyclic groups of $R^3$ may be mono-, di-, tri-, tetra-, or penta-substituted; or $R^3$ is an amino group mono- or di-substituted with members independently selected from alkyl, alkylcarbonyl, haloalkylcarbonyl, aryl, arylaminocarbonyl, arylalkylcarbonyl, arylalkoxycarbonyl, and 3-(2,2-dichloroethenyl)-2,2-dimethylcyclopropanecarbonyl;

(B) when X is oxygen, Z is fluorine and R is $C(O)R^1$, wherein $R^1$ is perfluoralkyl, phenyl or substituted phenyl, thienyl or substituted thienyl, furanyl or substituted furanyl, pyrollyl or substituted pyrollyl, or dihydrothiazolylthiomethyl; and (C) when X is nitrogen, R taken with the nitrogen is an isothiocyanate, succinimide, or saccharine group.

The compounds exhibit activity against plant nematodes and helminths that are indicators of animal anthelmintic activity and therefore are useful in agriculture and veterinary practice.

63 Claims, No Drawings

PESTICIDAL POLYHALOALKENE DERIVATIVES

RELATED APPLICATIONS

This application is a continuation-in-part of application Ser. No. 161,575, filed Feb. 29, 1988, now abandoned, which in turn is a continuation of application Ser. No. 870,055, filed Jun. 3, 1986, now abandoned, which in turn is a continuation-in-part of application Ser. No. 747,142, filed Jun. 20, 1985, now abandoned.

BACKGROUND OF THE INVENTION

This invention relates to pesticidal polyhaloalkene derivatives and use for combatting infestations of nematodes in soil and in plant systems, particularly agricultural crops, and for combatting plant-destructive diseases caused wholly or in part by nematodes. The invention further concerns anthelmintic applications of the compounds.

U.S. Pat. No. 3,513,172-Brokke and divisional patents thereof disclose nematicidal trifluorobutenyl derivatives of the formula $$F_2C=CFCH_2CH_2-R$$

where R is selected from various substituents including some heterocyclics. These and other patents reflect ongoing efforts of industry and governmental agencies to find and commercialize chemicals for combatting nematodes and nematode-induced plant diseases, to thereby reduce the substantial economic losses resulting from nematode infestations. U.S. Pat. No. 3,058,990 to Harman discloses bis-haloalkylthio-substituted thiadiazoles, but all of the Harman compounds are bis-substituted chloro and/or bromoalkylthio thiadiazoles which are excluded from the scope of the present invention.

SUMMARY OF THE INVENTION

A new class of polyhaloalkene derivatives has now been found having high nematicidal activity and good soil mobility. In addition, the compounds exhibit control of a variety of nematodes, and in some cases systemic activity. The compounds also are effective against helminths that are indicators of animal anthelmintic activity.

The novel nematicidal compounds of the invention are polyhaloalkene derivatives of the formula (I):
wherein X is sulfur, oxygen, or nitrogen, $Y^1$ and $Y^2$ are fluorine, Z is hydrogen or the same as $Y^1$ and $Y^2$, and n is 1-4; provided that:

(A) when X is sulfur, Z is fluorine and R is thienyl or substituted thienyl, thianaphthyl or substituted thianaphthyl, thiazolinyl or substituted thiazolinyl, oxadiazolyl or substituted oxadiazolyl, 3,4,4-trifluoro-3-butenyloxycarbonylmethyl, thiadiazolyl substituted by halogen or $R^2S$, wherein $R^2$ is 3,4,4-trifluoro-3-butenyl or $R^2$ is phenylmethyl or phenylthiomethyl each optionally substituted by halogen or nitro; or R is thiadiazolyl substituted by $R^3$, wherein $R^3$ is substituted aryl, arylalkyl, aryloxyalkyl, alkylthio, haloalkylthio, haloarylthio, cyanoalkylthio, arylalkylthio, aryloxyalkylthio, arylthioalkylthio, heterocycloalkylthio, alkenylthio, haloalkenylthio, halocycloalkylalkenylthio, wherein said aryl or heterocyclo substituents of $R^3$ may themselves be mono-, di-, tri-, tetra-, or penta-substituted; or $R^3$ is an amino group mono- or di- substituted with members independently selected from alkyl, alkylcarbonyl, haloalkylcarbonyl, aryl, arylaminocarbonyl, arylalkylcarbonyl, arylalkoxycarbonyl, and 3-(2,2-dichloroethenyl)-2,2-dimethylcyclopropanecarbonyl;

(B) when X is oxygen, Z is fluorine and R is $C(O)R^1$, wherein $R^1$ is perfluoralkyl, phenyl or substituted phenyl, thienyl or substituted thienyl, furanyl or substituted furanyl, pyrollyl or substituted pyrollyl, or dihydrothiazolylthiomethyl; and (C) when X is nitrogen, R taken with nitrogen is an isothiocyanate, succinimide, or saccharine group.

Other aspects of the invention include methods of controlling nematode populations and arresting plant diseases caused by nematodes, and nematicidal formulations based on the polyhaloalkene derivatives.

DETAILED DESCRIPTION

In subclasses A and B of the compounds of formula I above, available carbon atoms of the heterocyclic rings optionally may be substituted with any group or groups which are non-destructive of the nematicidal or anthelmintic activity of the compounds. Typical substituents include aliphatic, aromatic and heterocyclic groups, halo, nitro, cyano, alkoxy, alkylthio, haloalkyl, haloalkoxy, halo-, nitro-, cyano- or alkoxy- substituted phenyl, polyhaloalkenylthio, phenylalkylthio, phenylthioalkylthio, propargylthio, cycloalkylmethylthio, and the like, further including straight and branched chain structures, and the various isomers of such substituents.

Throughout this specification the alkyl, alkenyl and alkynyl groups may contain 1-11 or more carbon atoms and may be straight chain or branched. Cycloalkyl groups may contain 3-8 or more carbon atoms. Preferably, alkyl, alkenyl, alkynyl and alkoxy are lower alkyl, lower alkenyl, lower alkynyl or lower alkoxy, meaning that these groups contain 1-8 carbon atoms, more preferably 1-4 carbon atoms such as methyl, propenyl and methoxy. Halo or halogen means fluorine, chlorine, bromine or iodine, preferably fluorine, chlorine or bromine. Aromatic substituents include phenyl, naphthyl, anthracene, diphenyl, and the like.

Representative compounds of formula I are listed in Tables 1, 1a, 1b and 1c appended.

The preferred compounds of formula I are those of subclass A wherein R is defined as follows:

(1) R is a thiadiazolyl group of the structure:

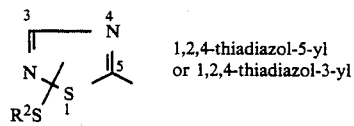

1,2,4-thiadiazol-5-yl or 1,2,4-thiadiazol-3-yl wherein $R^2$ is 3,4,4-trifluoro-3-butenyl, or a phenylmethyl or phenylthiomethyl group each optionally substituted with halogen or nitro. The $R^2S$- group may be in the 3- or 5-position of the 1,2,4-thiadiazole ring;

(2) R is a thiadiazolyl group as in (1) above but with iodo in place of $R^2S$;

(3) R is a thiadiazolyl group of the structure:

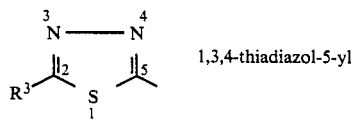

1,3,4-thiadiazol-5-yl wherein $R^3$ is substituted aryl, preferably phenyl, arylalkyl, aryloxyalkyl, alkylthio, haloalkylthio, haloarylthio, preferably chlorophenylthio, cyanoalkylthio, arylalkylthio, aryloxyalkylthio, arylthioalkylthio, heterocycloalkylthio, alkenylthio, haloalkenylthio, halocycloalkylalkenylthio, or an amino group mono- or disubstituted with members selected independently from alkyl, alkylcarbonyl, haloalkylcarbonyl, aryl, arylaminocarbonyl, arylalkylcarbonyl, arylalkoxycarbonyl and 3-(2,2-dichloroethenyl)-2,2-dimethylcyclopropanecarbonyl;

(4) R is an oxadiazolyl group of the structure:

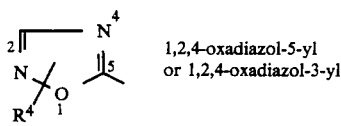

1,2,4-oxadiazol-5-yl or 1,2,4-oxadiazol-3-yl wherein $R^4$ is halo, aryl, substituted aryl, preferably phenyl, or arylalkyl optionally substituted with chloro, fluoro, alkyl, haloalkyl, alkoxy, or nitro. The $R^4$ group may be in the 3- or 5-position of the 1,2,4-oxadiazole ring; or (5) R is an oxadiazolyl group of the structure:

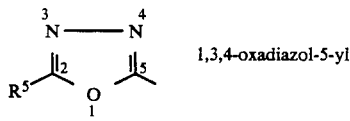

1,3,4-oxadiazol-5-yl wherein $R^5$ is halo, alkyl, haloalkyl, aryl, or substituted aryl, preferably phenyl, arylalkyl, aryloxyalkyl, arylthioalkyl, heterocycloalkyl, arylalkenyl or alkynyl ($C_2$–$C_{11}$).

The aryl and the heterocyclic groups described in (3) and (4) above are optionally substituted with one or more groups selected independently from halogen, alkyl, haloalkyl, alkoxy, haloalkoxy, cyano, nitro and phenyl, and the like. The aryl and heterocyclic groups described in (5) above are optionally substituted with one or more groups selected independently from halogen, alkyl, alkoxy, nitro, amino, hydroxy, acetyloxy and alkylaminocarbonyloxy, and the like.

Among the substituted thiadiazolyl and oxadiazolyl groups which may be employed in (3), (4), and (5) above are those comprising substituted aryl or heterocyclyl thiadiazoles or oxadiazoles, preferably substituted phenyl groups, including mono-, di-, tri-, tetra-, and penta-substituted phenyl where said substituents may be the same or different.

Included among such groups which may be used are 2-, 3-, or 4- mono-substituted phenyl moieties where the phenyl substituent may desirably be chloro, bromo, fluoro, iodo, trifluoromethyl, nitro, cyano, methylthio, methylsulfinyl, methylsulfoxy, methyl, isopropyl, t-butyl, methoxy, ethoxy, trifluoromethoxy, tetrafluoroethoxy, dimethylamino, phenoxy, phenyl, and the like.

Di-substituted phenyl groups include 2,3-, 2,4-, 2,5-, 2,6-, 3,4-, or 3,5-difluorophenyl, -dichlorophenyl, or -dimethylphenyl. These substituents may be the same or different. Examples of the latter are 2-fluoro-6-chlorophenyl, 3-fluoro-4-methoxyphenyl, 2-fluoro-3-methylphenyl, 2-fluoro-3-methoxyphenyl, 3-methoxy-4-fluorophenyl, 2-methyl-3-biphenyl, 3-phenoxy-4-fluorophenyl, and 2-fluoro-3-biphenyl, and the like.

Tri-substituted phenyl groups include 2,3,4-, 2,4,6-, 2,4,5-, 3,4,5-, 2,3,5- and 2,3,6-trichlorophenyl, trifluorophenyl, and -trimethylphenyl. These substituents may be the same or different. Examples of the latter are (2,4-dichloro[1,1'-biphenyl]-3-yl), (2,4-difluoro[1,1'-biphenyl]-3-yl), (2,4-dimethyl[1,1'-biphenyl]-3-yl), and the like.

Tetra-substituted phenyl groups include 2,3,4,5-, 2,3,5,6-, 2,3,4,6-tetrafluorophenyl, -tetrachlorophenyl, -tetramethylphenyl and the like. These substituents may also be the same or different, in a like manner to those above.

Penta-substituted phenyl groups may also be employed, as for example 2,3,4,5,6-pentachlorophenyl or -pentafluorophenyl and the like. Alternatively, different groups may be employed, as above, for example 2,3,5,6-tetrafluoro-4-methylphenyl, 2,3,5,6-tetrafluoro-4-methoxyphenyl and the like.

Also preferred amongst the $R^4$ and $R^5$- substituted compounds above are those where $R^4$ is a nuclear 3- or 5-halo-substituted-1,2,4-oxadiazole and $R^5$ is a nuclear 2-or 5-halo-substituted-1,3,4-oxadiazole. These compounds may readily be prepared in various ways, using the desired halo-substituted reactants.

For example, glyoxylic acid may be reacted with hydroxylamine hydrochloride in an aqueous medium, forming the corresponding oxime. This oxime is then reacted with chlorine in aqueous methylene chloride to form dichloroformaldoxime. Treatment of dichloroformaldoxime with silver nitrate in the presence of cyanogen chloride produces 3,5-dichloro-1,2,4-oxadiazole. If cyanogen bromide is substituted for cyanogen chloride, the product recovered is 5-bromo-3-chloro-1,2,4-oxadiazole. The final product, 3-chloro-5-(3,4,4-trifluoro-3-buten-1-ylthio)-1,2,4-oxadiazole, may be produced by reacting the dihalo-1,2,4-oxadiazole with lithium metal, then with elemental sulfur, and finally with 4-bromo-1,2,2-trifluoro-1-butene. An alternate final step involves the reaction of 3,4,4-trifluoro-3-butene-1-thiol with 5-halo-3-chloro-1,2,4-oxadiazole. Preparation of 3,4,4-trifluoro-3-butene-1-thiol may be accomplished by reacting 4-bromo-1,1,2-trifluoro-1-butene with magnesium metal to form 3,4,4-trifluoro-3-buten-1-ylmagnesium bromide. This Grignard reagent is then reacted with elemental sulfur in diethyl ether to form the desired 3,4,4-trifluoro-3-butene-1-thiol. In a like manner, the corresponding 2-or 5-halo-substituted 1,3,4-oxadiazole may be prepared.

Synthesis

The compounds of formula I are prepared in a known manner. For example, a polyhaloalkene such as 4-bromo-1,1,2-trifluoro-1-butene is reacted with a mercaptothiazoline in a reaction solvent medium containing sodium ethoxide to form the thiothiazoline derivative of the polyhaloalkene. Examples 1, 2, and 8–14 below are representative of this and other reaction schemes for synthesis of the subclass A compounds of formula I (X=sulfur). Compounds of formula I wherein X is oxygen (subclass B) may be prepared as described in Examples 3 and 4. Similarly, the subclass C (X=nitrogen) is prepared as described in Examples 5 and 6.

Other polyhaloalkenes may be used in known ways to prepare other compounds of formula I. For example, trifluoroethylene can be chain-extended with methyl dibromide and the 1,3-dibromo-1,2,2-trifluoropropane product then reacted with a mercaptan to form a thio intermediate. The intermediate is then converted, as follows, wherein "BP" is benzoyl peroxide and "DBU"

is 1,8-diazabicyclo[5.4.0]undec-7-ene catalyst, as described by Tarrant and Tandon, J. Org. Chem. 34(4), 864 (1969):

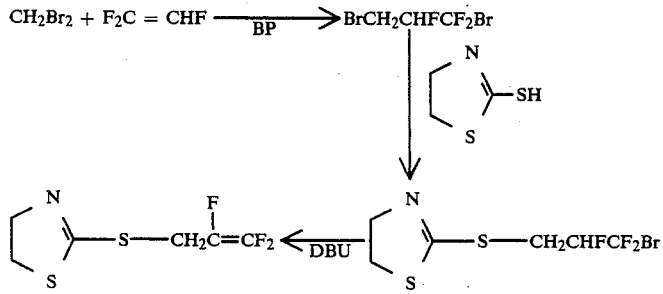

Dihalopropene derivatives within the scope of formula I may be prepared by the following general reaction, wherein $Y^1$ and $Y^2$ are as defined above and one of $Y^1$ and $Y^2$ also may be hydrogen:

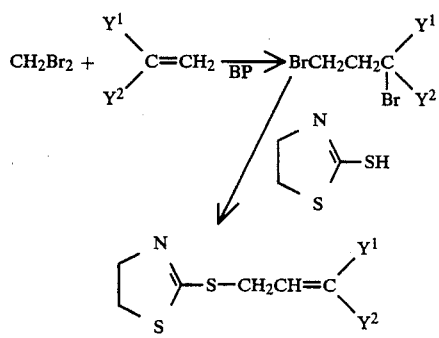

Trihalopropene derivatives also may be prepared in a manner and reaction similar to the Tarrant and Tandon scheme to form other compounds of formula I, wherein $Y^1$, $Y^2$ and Z are as defined in formula I:

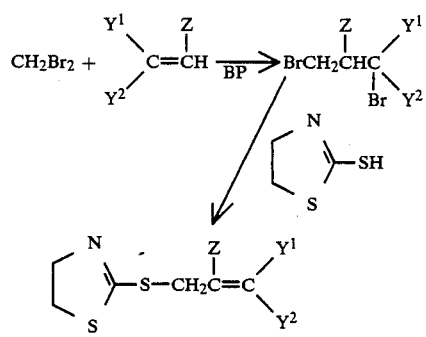

Methods of preparing propenes, butenes and other alkenes having mixed halogen substituents and therefore useful in the invention for preparing compounds of formula I are described in a Ph.D. thesis of M. R. Lillyguist, University of Florida (1955), pages 9, 39, 59 and 60. It will be apparent, therefore, that the polyhaloalkenes and heterocyclic or other compounds used to prepare the compounds of formula I generally are known materials or can be synthesized by known procedures.

The following examples further describe methods of preparing the compounds of the invention. In the examples all parts and percentages are by weight and all temperatures are ° C. unless otherwise stated. The products of Examples 1-9 correspond to compounds 1-9 listed in Tables 1 and 1b. Examples 10-15 identify the tabulated compounds to which they relate.

EXAMPLE 1

2-(3,4,4-Trifluoro-3-butenylthio)-4,5-dihydrothiazole

Sodium ethoxide was prepared by stirring 0.25 gram (0.011 mole) of sodium metal in 30 ml of absolute ethanol. To this was added 1.2 grams (0.01 mole) of 2-mercaptothiazoline. The reaction mixture was stirred for one hour and the excess ethanol was removed under reduced pressure. The residue was dissolved in 35 ml of methyl ethyl ketone and 2.0 grams (0.01 mole) of 4-bromo-1,1,2-trifluoro-1-butene was added. The reaction mixture was stirred at ambient temperature for four hours, then concentrated under reduced pressure to a residue. The residue was dissolved in 50 ml of toluene and washed with three 25 ml portions of water. The organic layer was dried with sodium sulfate and filtered. The filtrate was concentrated under reduced pressure to give 1.7 grams of 2-(3,4,4-trifluoro-3-butenylthio)-4,5-dihydrothiazole as an oil. The nmr and the ir spectra were consistent with the proposed structure.

EXAMPLE 2

5-Methylthio-2-(3,4,4-trifluoro-3-butenylthio)-1,3,4-thiadiazole

A solution of 2.0 grams (0.012 mole) of 2-mercapto-5-methylthio-1,3,4-thiadiazole in 25 ml of distilled acetone was added to a stirred mixture of 0.84 gram (0.006 mole) of potassium carbonate and 0.2 gram (0.001 mole of potassium iodide in 25 ml of distilled acetone. With continued stirring 2.2 grams (0.012 mole) of 4-bromo-1,1,2-trifluoro-1-butene was added dropwise. Upon completion of addition the reaction mixture was heated under reflux for four hours.

The reaction mixture was cooled, filtered, and the filtrate concentrated under reduced pressure to a residue. The residue was dissolved in diethyl ether and washed with aqueous 5% sodium hydroxide. The organic layer was dried with magnesium sulfate and filtered. The filtrate was concentrated under reduced pressure to give 1.3 grams of 5-methylthio-2-(3,4,4-trifluoro-3-butenylthio)-1,3,4-thiadiazole as an oil. The nmr and the ir spectra were consistent with the proposed structure.

EXAMPLE 3

(3,4,4-Trifluoro-3-butenyl) heptafluorobutyrate (A) A stirred solution of 2.6 ml (0.02 mole) of heptafluorobutyric acid in 50 ml of water was warmed to 50°

C. and 5.1 grams (0.022 mole) of silver oxide was added. Upon completion of addition the reaction mixture temperature was maintained at 50°–60° C. for two hours. The reaction mixture was allowed to cool to ambient temperature, then it was filtered. The filtrate was concentrated under reduced pressure to give 6.4 grams of the silver salt of heptafluorobutyric acid as a solid.

(B) To a stirred mixture of 3.2 grams (0.01 mole) of the silver salt of heptafluorobutyric acid in 40 ml of diethyl ether was added dropwise 1.9 grams (0.01 mole) of 4-bromo-1,1,2-trifluoro-1-butene in 10 ml of diethyl ether. Upon completion of addition the reaction mixture was stirred for two hours at ambient temperature, then was heated under reflux for one hour. The ether solvent was removed by distillation and the residual oil distilled under reduced pressure to give 1.0 gram of (3,4,4-trifluoro-3-butenyl) heptafluorobutyrate; b.p. 25° C./4.0 mm Hg. The nmr spectrum was consistent with the proposed structure.

EXAMPLE 4

(3,4,4-Trifluoro-3-butenyl) 4-chlorobenzoate

To a stirred solution of 1.6 grams (0.01 mole) of 4-chlorobenzoic acid in 35 ml of acetonitrile was added 1.5 ml (0.01 mole) of 1,8-diazabicyclo[5.4.0]-undec-7-ene, followed by 1.9 grams (0.01 mole) of 4-bromo-1,1,2-trifluoro-1-butene. The reaction mixture was heated under reflux for four hours then allowed to cool to ambient temperature. Water, 25 ml, was added to the reaction mixture, and the reaction mixture was extracted with three 20 ml portions of diethyl ether. The combined extracts were washed in succession with one 25 ml portion of water, two 25 ml portions of aqueous 5% sodium hydroxide and, finally, one 25 ml portion of water. The organic layer was dried with sodium sulfate and filtered. The filtrate was concentrated under reduced pressure to give 1.2 grams of (3,4,4-trifluoro-3-butenyl) 4-chlorobenzoate as an oil. The nmr and the ir spectra were consistent with the proposed structure.

EXAMPLE 5

N-(3,4,4-trifluoro-3-butenyl)succinimide

This compound was prepared in a manner analogous to that of Example 1 using 1.1 grams (0.01 mole) of succinimide, 1.9 grams (0.01 mole) of 4-bromo-1,1,2-trifluoro-1-butene, 0.25 gram (0.01 mole) of sodium metal, 30 ml of absolute ethanol and 20 ml of dimethylformamide. The yield of N-(3,4,4-trifluoro-3-butenyl)succinimide was 0.3 gram as an oil. The nmr and the ir spectra were consistent with the proposed structure.

EXAMPLE 6

(3,4,4-Trifluoro-3-butenyl)isothiocyanate (A) To a stirred solution of 10.0 grams (0.053 mole) of 4-bromo-1,1,2-trifluoro-1-butene in 50 ml of dimethylformamide was added 10.4 grams (0.056 mole) of the commercially available potassium salt of phthalimide. The reaction mixture was warmed to 50° C. where it stirred for four hours. The reaction mixture was allowed to cool and 50 ml of chloroform was added. The mixture was poured into 200 ml of water. The aqueous layer was separated and extracted with two 50 ml portions of chloroform. The combined organic layers were washed with two 50 ml portions of aqueous 5% sodium hydroxide and one 50 ml portion of water. The organic layer was dried with sodium sulfate and filtered. The filtrate was concentrated under reduced pressure to give 4.8 grams of N-(3,4,4-trifluoro-3-butenyl)phthalimide as an oil. The nmr spectrum was consistent with the proposed structure.

(B) A stirred solution of 4.2 grams (0.016 mole) of N-(3,4,4-trifluoro-3-butenyl)phthalimide and 1.0 ml (0.032 mole) of anhydrous hydrazine in 50 ml of methanol was heated under reflux for one hour. The reaction mixture was allowed to cool and the solvent removed under reduced pressure. The residue was taken up in 25 ml of water and 30 ml of concentrated hydrochloric acid. The reaction mixture was heated under reflux for two hours and then cooled to 0° C. A solid was removed from the reaction mixture by filtration. The filtrate was concentrated under reduced pressure to a residue. The residue was taken up in 50 ml of water and made basic with aqueous 10% sodium hydroxide. The mixture was extracted with two 25 ml portions of diethyl ether. The combined extracts were dried with sodium sulfate and filtered. The filtrate was concentrated under reduced pressure to give 0.4 gram of 4-amino-1,1,2-trifluoro-1-butene as an oil. The ir spectrum was consistent with the proposed structure.

(C) A stirred solution of 0.4 gram (0.004 mole) of 4-amino-1,1,2-trifluoro-1-butene in 25 ml of diethyl ether was saturated with gaseous hydrochloric acid. The reaction mixture was concentrated under reduced pressure to give 0.4 gram of 4-amino-1,1,2-trifluoro-1-butene hydrochloride as a solid. The nmr spectrum was consistent with the proposed structure.

(D) To a stirred solution of 0.4 gram (0.0027 mole) of 4-amino-1,1,2-trifluoro-1-butene hydrochloride in 15 ml of chloroform was added 0.3 gram (0.003 mole) of thiophosgene, followed by 0.7 ml (0.009 mole) of triethylamine. Upon completion of addition the reaction mixture was stirred at ambient temperature for three hours. The reaction mixture was then washed in succession with one 25 ml portion of water, two 25 ml portions of aqueous 5% sodium hydroxide, and, finally, one 25 ml portion of water. The organic layer was dried with sodium sulfate and filtered. The filtrate was concentrated under reduced pressure to give 0.3 gram of (3,4,4-trifluoro-3-butenyl) isothiocyanate as an oil. The ir spectrum was consistent with the proposed structure.

EXAMPLE 7

4,5,5-Trifluoro-4-penten-1-ol (A) To a stirred mixture of 2.4 grams (0.1 mole) of magnesium turnings in 100 ml of diethyl ether was added 18.9 grams (0.1 mole) of 4-bromo-1,1,2-trifluoro-1-butene. Upon completion of addition the reaction mixture was heated under reflux until the reaction was complete. The reaction mixture was cooled to 0° C. and 9.0 grams (0.2 mole) of carbon dioxide was bubbled in slowly. Upon completion of addition the reaction mixture was stirred for one hour, then 100 ml of aqueous 20% hydrochloric acid was added to destroy the excess magnesium. The reaction mixture was extracted with three 40 ml portions of diethyl ether. The combined extracts were cooled and 40 ml of aqueous 25% sodium hydroxide was added slowly. The organic layer was separated and extracted with one 40 ml portion of aqueous 25% sodium hydroxide. The combined base layers were cautiously acidified with aqueous 20% hydrochloric acid. The mixture was extracted with two 100 ml portions of diethyl ether. The combined extracts were dried with sodium sulfate and filtered. The filtrate was concentrated under reduced pressure to give 6.9 grams of 4,5,5-trifluoro-4-pentenoic acid as an oil. The nmr and ir spectra were consistent with the proposed structure.

(B) To a stirred suspension of 0.4 gram (0.01 mole) of lithium aluminum hydride in 20 ml of diethyl ether was added dropwise a solution of 1.5 grams (0.01 mole) of 4,5,5-trifluoro-4-pentenoic acid in 30 ml of diethyl ether. Upon completion of addition the reaction mixture was stirred at ambient temperature for one hour, then 20 ml of water was added carefully. The mixture was filtered and the filtrate concentrated under reduced pressure to give 0.8 gram of 4,5,5-trifluoro-4-penten-1-ol as an oil. The nmr and the ir spectra were consistent with the proposed structure.

EXAMPLE 8

3-Chloro-5-(3,4,4-trifluoro-3-butenylthio)-1,2,4-thiadiazole (A) A stirred solution of 5.0 grams (0.026 mole) of dipotassium cyanoimidodithiocarbonate [prepared by the method of L. S. Wittenbrook et al, J. Org. Chem., 38, 3, 465 (1973)] in 19 ml of acetone and 22 ml of water was cooled to 0° C. and 4.9 grams (0.026 mole) of 4-bromo-1,1,2-trifluoro-1-butene in 10 ml of acetone was added dropwise. Upon completion of addition the reaction mixture was allowed to warm to ambient temperature where it stirred for 16 hours. The reaction mixture was concentrated under reduced pressure to a residual solid. The solid was dissolved in ethyl acetate and filtered. The filtrate was concentrated under reduced pressure, and the residual solid dried in a vacuum oven. The dried solid was dissolved in hot chloroform - ethyl acetate and filtered. The filtrate was concentrated under reduced pressure, and the residual solid dried in a vacuum oven to give 4.4 grams of potassium (3,4,4-trifluoro-3-butenyl) cyanoimidodithiocarbonate. The nmr spectrum was consistent with the proposed structure.

(B) A stirred solution of 2.0 grams (0.008 mole) of potassium (3,4,4-trifluoro-3-butenyl) cyanoimidodithiocarbonate in 10 ml of chloroform was cooled to 0° C. and 1.2 grams (0.009 mole) of sulfuryl chloride was added dropwise. Upon completion of addition the reaction mixture was maintained at 0° C. for one hour, warmed under reflux for 4 hours, then at ambient temperature for 16 hours. Stirring was continued throughout the 21 hour period. The reaction mixture was filtered and the filtrate concentrated under reduced pressure. The concentrate was passed through silica gel using diethyl ether as an eluent. The ether eluate was filtered and the filtrate concentrated under reduced pressure to a residual oil. The oil was dried in a vacuum oven to give 0.9 gram of 3-chloro-5-(3,4,4-trifluoro-3-butenylthio)-1,2,4-thiadiazole. The nmr and the ir spectra were consistent with the proposed structure.

EXAMPLE 9

3-Bromo-5-(3,4,4-trifluoro-3-butenylthio)-1,2,4-thiadiazole

A stirred solution of 3.0 grams (0.011 mole) of potassium (3,4,4-trifluoro-3-butenyl) cyanoimidodithiocarbonate (prepared as in Example 8, Step A) in 25 ml of water was cooled to 0° C. and 2.2 grams (0.014 mole) of bromine was added dropwise under a positive gaseous nitrogen pressure. Upon completion of addition the reaction mixture temperature was maintained at 0° C. for one hour, then was allowed to warm to ambient temperature where it stirred for 16 hours. Sodium thiosulfate was added to the reaction mixture, which was then partitioned between chloroform and additional water. The chloroform layer was separated and dried with magnesium sulfate. The mixture was filtered and concentrated under reduced pressure to a residual oil. The oil was passed through silica gel using 4:1-hexane:diethyl ether as an eluent. The eluate was concentrated under reduced pressure to give 1.1 grams of 3-bromo-5-(3,4,4-trifluoro-3-butenylthio)-1,2,4-thiadiazole as an oil. The nmr spectrum was consistent with the proposed structure.

EXAMPLE 10

Compound 25

3,5-Di(3,4,4-Trifluoro-3-butenylthio)-1,2,4-thiadiazole (A) A stirred solution of 16.0 grams (0.08 mole) of dipotassium cyanoimidodithiocarbonate (prepared as in Example 8, Step A) and 2.6 grams (0.08 mole) of sulfur in 425 ml of methanol was heated under reflux for 15 minutes. The reaction mixture was allowed to cool then was concentrated under reduced pressure to a residual solid. The solid was dried under reduced pressure to yield 18.1 grams of the dipotassium salt of 3,5-dimercapto-1,2,4-thiadiazole.

(B) A solution of 1.0 gram (0.004 mole) of the dipotassium salt of 3,5-dimercapto-1,2,4-thiadiazole in 35 ml of methyl ethyl ketone was stirred and 1.7 grams (0.009 mole) of 4-bromo-1,1,2-trifluoro-1-butene was added. The reaction mixture was heated under reflux for two hours then allowed to cool to ambient temperature where it stirred for 18 hours. The reaction mixture was concentrated under reduced pressure lo a residue. The residue was stirred in 25 ml of water and the mixture was extracted with two 25 ml portions of toluene. The organic layer was dried with sodium sulfate and filtered. The filtrate was concentrated under reduced pressure to yield 1.1 grams of 3,5-di-(3,4,4-trifluoro-3-butenylthio)-1,2,4-thiadiazole as a liquid. The nmr spectrum was consistent with the proposed structure.

EXAMPLE 11

Compound 26

3-(4-Nitrophenylmethylthio)-5-(3,4,4-trifluoro-3-butenylthio)-1,2,4-thiadiazole (A) A stirred solution of 24.7 grams (0.109 mole) of the dipotassium salt of 3,5-dimercapto-1,2,4-thiadiazole (prepared as in Example 10, Step A) in 200 ml of water was acidified with concentrated hydrochloric acid. The resultant solid was collected by filtration to yield 17.3 grams of wet 5-amino-1,2,4-dithiazol-3-thione; m.p. 217°–220° C.

(B) A solution of 2.2 grams (0.055 mole) of sodium hydroxide in 7 ml of water and 20 ml of ethanol was stirred and 4.0 grams (0.027 mole) of 5-amino-1,2,4-dithiazol-3-thione was added portionwise. After all of the 5-amino intermediate was in solution, 4.7 grams (0.027 mole) of 4-nitrophenylmethyl chloride was added dropwise. Upon completion of addition the reaction mixture was stirred at ambient temperature for 16 hours. The reaction mixture was concentrated under reduced pressure to a residue. The residue was dissolved in 20 ml of water then extracted with two 25 ml portions of diethyl ether. The aqueous layer was acidified with concentrated hydrochloric acid to yield a gummy solid. The solid was extracted from the aqueous layer with two 25 ml portions of ethyl acetate. The combined extracts were dried with sodium sulfate and filtered. The filtrate was concentrated under reduced pressure to yield a gummy solid. The solid was dissolved in methylene chloride and filtered to remove a small amount of insoluble material. The filtrate was concentrated under reduced pressure to yield 2.8 grams of 3-(4-nitrophenylmethylthio)-5-mercapto-1,2,4-thiadiazole as a solid. The nmr spectrum was consistent with the proposed structure.

(C) A solution of 0.25 gram (0.011 mole) of sodium in 35 ml of ethanol was stirred and 2.7 grams (0.0095 mole) of 3-(4-nitrophenylmethylthio)-5-mercapto-1,2,4-thiadiazole was added. Upon completion of addition the reaction mixture was stirred at ambient temperature for one hour. The ethanol solvent was removed under reduced pressure. The residue was dissolved in 35 ml of methyl ethyl ketone and 1.6 grams (0.0085 mole) of 4-bromo-1,1,2-trifluoro-1-butene was added. Upon completion of addition the reaction mixture was stirred for 16 hours, then was concentrated under reduced pressure to a residue. The residue was dissolved in 50 ml of toluene and washed with 25 ml of water, two 25 ml portions of aqueous 5% sodium hydroxide solution, and 25 ml of water. The organic layer was dried with sodium sulfate and filtered. The filtrate was concentrated under reduced pressure to yield a residual oil. The oil was dissolved in methylene chloride and passed through a column of silica gel. The eluate was concentrated under reduced pressure to yield 2.1 grams of 3-(4-nitrophenylmethylthio)-5-(3,4,4-trifluoro-3-butenylthio)-1,2,4-thiadiazole. The nmr spectrum was consistent with the proposed structure.

EXAMPLE 12

Compound 30

2-(1-Methylethylthio)-5-(3,4,4-trifluoro-3-butenylthio)-1,3,4-thiadiazole

A solution of 22.5 grams (0.15 mole) of 2,5-dimercapto-1,3,4-thiadiazole in 200 ml of tetrahydrofuran was stirred and 21 ml (0.15 mole) of triethylamine was added dropwise. Upon completion of addition the reaction mixture was stirred at ambient temperature for 15 minutes, then 28.4 grams (0.15 mole) of 4-bromo-1,1,2-trifluoro-1-butene was added dropwise. Upon completion of addition the reaction mixture was heated under reflux for two hours. The cooled reaction mixture was concentrated under reduced pressure to a residue. The residue was stirred in 250 ml of diethyl ether and extracted with two 100 ml portions of aqueous 10% potassium hydroxide. The combined extracts were acidified with aqueous 10% hydrochloric acid, then were extracted with two 100 ml portions of diethyl ether. The combined ether extracts were dried with sodium sulfate and filtered. The filtrate was concentrated under reduced pressure to yield, after drying, 35.6 grams of 2-mercapto-5-(3,4,4-trifluoro-3-butenylthio)-1,3,4-thiadiazole as a solid. The nmr spectrum was consistent with the proposed structure.

(B) In a manner analogous to Example 11, Step C, 1.3 grams (0.005 mole) of 2-mercapto-5-(3,4,4-trifluoro-3-butenylthio)-1,3,4-thiadiazole, 0.5 ml (0.005 mole) of 2-iodopropane, 0.15 gram (0.007 mole) of sodium were reacted in 35 ml of ethanol and 35 ml of methyl ethyl ketone by heating the mixture under reflux for five hours prior to stirring at ambient temperature for 16 hours. The yield of 2-(1-methylethylthio)-5-(3,4,4-trifluoro-3-butenylthio)-1,3,4-thiadiazole was 1.3 grams as a liquid. The nmr spectrum was consistent with the proposed structure.

EXAMPLE 13

Compound 37

2-(4-Chlorophenyl)-5-(3,4,4-trifluoro-3-butenylthio)-1,3,4-thiadiazole (A) A stirred solution of 8.1 grams (0.048 mole) of 4-chlorobenzoic acid hydrazide in 300 ml of triethyl orthoformate was heated under reflux for 16 hours. The excess triethyl orthoformate was removed by distillation and the residual solid was stirred with petroleum ether to yield 7.7 grams of 2-(4-chlorophenyl)-1,3,4-oxadiazole; m.p. 129° C. The nmr spectrum was consistent with the proposed structure.

(B) Under a nitrogen atmosphere, a solution of 17 grams (0.084 mole) of phosphorus pentasulfide in 100 ml of dry xylene was stirred and 7.6 grams (0.042 mole) of 2-(4-chlorophenyl)-1,3,4-oxadiazole was added. Upon completion of addition the reaction mixture was heated under reflux for 30 hours. The reaction mixture was cooled and 100 ml of water was added dropwise. The mixture was filtered through diatomaceous earth to separate the organic and aqueous phases. The organic phase (the filtrate) was extracted with an aqueous 10% potassium hydroxide solution. The extract was acidified with an aqueous 5% hydrochloric acid solution, and then was extracted with diethyl ether. The ether extract was concentrated under reduced pressure to yield 0.3 gram of 2-(4-chlorophenyl)-5-mercapto-1,3,4-thiadiazole; m.p. 178° C.

(C) In a manner analogous to Example 2, 0.3 gram (0.0015 mole) of 2-(4-chlorophenyl)-5-mercapto-1,3,4-thiadiazole, 0.4 gram (0.002 mole) of 4-bromo-1,1,2-trifluoro-1-butene, 0.2 gram (0.0015 mole) of potassium carbonate, and 0.05 gram of potassium iodide were reacted in 9 ml of methyl ethyl ketone. The yield of 2-(4-chlorophenyl)-5-(3,4,4-trifluoro-3-butenylthio)-1,3,4-thiadiazole was 0.1 gram; m.p. 68°-69° C. The nmr spectrum was consistent with the proposed structure.

EXAMPLE 14

Compound 39

3-(4-Chlorophenyl)-5-(3,4,4-trifluoro-3-butenylthio)-1,2,4-oxadiazole (A) A stirred solution of 4.1 grams (0.03 mole) of 4-chlorobenzonitrile, 2.1 grams (0.03 mole) of hydroxylamine hydrochloride, and 2.1 grams (0.015 mole) of potassium carbonate in 10 ml of water and 100 ml of ethanol was heated under reflux for 16 hours. The reaction mixture was cooled and 50 ml of water was added. The ethanol solvent was removed under reduced pressure. The concentrate was cooled in an ice bath and the resultant solid collected by filtration. The solid was dried to yield 4.4 grams of N-hydroxyimido-4-chlorobenzamide; m.p. 122°-130° C.

(B) A solution of 4.4 grams (0.028 mole) of N-hydroxyimido-4-chlorobenzamide in 50 ml of diethyl ether was stirred and 0.55 ml (0.007 mole) of thiophosgene was added dropwise. Upon completion of addition the reaction mixture was stirred at ambient temperature for 15 minutes then was heated under reflux for one hour. The reaction mixture was cooled and filtered to collect bis 0,0'-thiocarbonyl(4-chloro-N-hydroxybenzenecarboximidamide). A 100% yield was assumed.

(C) A solution of 10.0 grams (0.25 mole) of sodium hydroxide in 90 ml of water was stirred and 5.4 grams (0.14 mole) of bis 0,0'-thiocarbonyl(4-chloro-N-hydroxybenzenecarboximidamide) was added. Upon completion of addition the reaction mixture was heated under reflux for one hour. The reaction mixture was cooled and extracted with two 50 ml portions of diethyl ether. The aqueous layer was acidified with concentrated hydrochloric acid. The resultant precipitate was collected by filtration, washed with water, and dried to yield 1.0 gram of 3-(4-chlorophenyl)-5-mercapto-1,2,4-oxadiazole; m.p. 139°-156° C., dec. The nmr spectrum was consistent with the proposed structure.

(D) In a manner analogous to Example 2, 0.7 gram (0.003 mole) of 3-(4-chlorophenyl)-5-mercapto-1,2,4-oxadiazole, 0.6 gram (0.003 mole) of 4-bromo-1,1,2-trifluoro-1-butene, 0.2 gram (0.0015 mole) of potassium carbonate, and 0.1 gram of potassium iodide were reacted in 40 ml of distilled acetone. The yield of 3-(4-chlorophenyl)-5-(3,4,4-trifluoro-3-butenylthio)-1,2,4-oxadiazole was 0.3 gram; m.p. 49°-52° C. The nmr spectrum was consistent with the proposed structure.

EXAMPLE 15

Compound 43

5-(3-4,4-Trifluoro-3-butenylthio)-1,3,4-oxadiazole (A) A solution of 25 grams (0.147 mole) of 4-chlorophenylacetic acid in 250 ml of acetonitrile was stirred and 15.0 grams (0.0147 mole) of bromoethane, followed by 22.0 grams (0.147 mole) of 1,8-diazabicyclo[5.4.0]undec-7-ene, were added. Upon completion of addition the reaction mixture was cooled in a water bath while being stirred for 18 hours. The reaction mixture was concentrated under reduced pressure to one-half volume and then was added to 50 ml of water. The mixture was extracted with two portions of diethyl ether. The combined extracts were dried with magnesium sulfate and filtered. The filtrate was concentrated under reduced pressure to yield 18.2 grams of ethyl (4-chlorophenyl)acetate.

(B) A stirred solution of 18.2 grams (0.091 mole) of ethyl (4-chlorophenyl)acetate and 10 ml of hydrazine hydrate in 10 ml of ethanol was heated under reflux for one hour during which time a solid precipitated. The solid was collected by filtration to yield, when dried, 14.9 grams of 4-chlorophenylacetic acid hydrazide; m.p. 159°-161° C. The nmr spectrum was consistent with the proposed structure.

(C) A stirred solution of 7.0 grams (0.038 mole) of 4-chlorophenylacetic acid hydrazide, 3.0 grams (0.039 mole) of carbon disulfide and 2.8 grams (0.050 mole) of potassium hydroxide in 10 ml of water and 200 ml of ethanol was heated under reflux for four hours. The ethanol was removed under reduced pressure. The concentrate was taken up in water and the mixture washed with diethyl ether. The aqueous layer was acidified with aqueous 5% hydrochloric acid and then was extracted with diethyl ether. The extract was dried with magnesium sulfate and filtered. The filtrate was concentrated under reduced pressure to yield 3.9 grams of 2-(4-chlorophenylmethyl)-5-mercapto-1,3,4-oxadiazole; m.p. 115° C. The nmr spectrum was consistent with the proposed structure.

(D) In a manner analogous to Example 2, 2.4 grams (0.011 mole) of 2-(4-chlorophenylmethyl)-5-mercapto-1,3,4-oxadiazole, 2.0 grams (0.011 mole) of 4-bromo-1,1,2-trifluoro-1-butene, 1.5 grams (0.011 mole) of potassium carbonate and 0.5 gram of potassium iodide were reacted in 45 ml of acetone. The yield of 2-(4-chlorophenylmethyl)-5-(3,4,4-trifluoro-3-butenylthio)-1,3,4-oxadiazole was 1.5 grams as a liquid. The nmr spectrum was consistent with the proposed structure.

The appended Tables 1, 1a, 1b and 1c list compounds prepared as in the foregoing Examples. In Tables 1a and 1c the compounds are those of formula I wherein $Y^1$, $Y^2$ and Z are fluoro, based upon the use of 4-bromo-1,1,2-trifluoro-1-butene as the starting material in the synthesis.

Pesticidal Use

The compounds of the invention can be used against a variety of pests that attack plants and animals. In agriculture, they are useful as nematicides, particularly against plant-parasitic nematodes and "free-living" nematodes, i.e., nematodes not dependent on any specific plant or other host. An example of the latter is the microbivorous nematode *Caenorhabditis elegans*. This nematode will feed on bacteria such as *Escherichia coli* and is used as a screen for both agricultural and veterinary nematicides or anthelmintics.

When used as anthelmintics, in veterinary treatments for treatment of infestations of *Ascaris lumbricoides* (roundworm in pigs) for example, the compounds may be administered orally, parenterally or topically either alone but more usually in a pharmaceutically acceptable carrier, to provide an appropriate dosage. Such carriers include one or more of water, gelatine, sugars, starches, organic acids such as stearic or citric acid and salts thereof, talc, vegetable fats or oils, gums, glycols and other excipients, for administration as solids (e.g., tablets or capsules) or liquids (e.g., solutions, suspensions or emulsions). The compositions may also contain preservatives, stabilizers, wetting or emulsifying agents, buffers, salts and other therapeutic agents. The compositions may be formulated by conventional methods to contain about 5 to 95% by weight of the anthelmintic compound, preferably about 25 to 75% by weight. Further guidance to anthelmintic activity, formulations and modes of treatment, utilizing the compounds of the invention, is available from publications on the subject, such as the article "Chemotherapeutics, Anthelmintic" in Kirk-Othmer, Encyclopedia of Chemical Technology, Third ed., 5 451–468, and articles cited therein, and in the patent literature, such as U.S. Pat. No. 3,576,892, col. 3, lines 29–56.

In using the compounds of the invention as agricultural nematicides, the compounds, like most agricultural chemicals, are generally not applied full strength, but are formulated with agriculaturally acceptable carriers and various additives normally employed for facilitating the dispersion of active ingredients, optionally with other active ingredients, recognizing that the formulation and mode of application of a toxicant may affect the activity of the material. The present compounds may be applied, for example, as powders or liquids, the choice of application varying with the nematode species and environmental factors present at the particular locus of infestation. Thus, the compounds may be formulated as granules, dusts, wettable powders, emulsifiable concentrates, solutions, suspensions, dispersions, controlled release compositions, and the like.

A typical formulation may vary widely in concentration of the active ingredient depending on the particular agent used, additives, carriers or other active ingredients used, the nematode species to be controlled, and the desired mode of application. With due consideration to these factors, the active ingredient of a typical formulation may, for example, suitably be present at a concentration of from about 0.5% up to about 99.5% by weight of the formulation. Surface active agents, if employed in the formulation, may be present at various concentrations, suitably in the range of 1 to 30% by weight.

Dusts are admixtures of the active ingredient with finely divided solid carriers and/or diluents such as talc, natural clays, kieselguhr, pyrophyllite, chalk, diatomaceous earths, calcium phosphates, calcium and magnesium carbonates, sulfur, lime, flours, and other organic and inorganic solid carriers. These finely divided formulations generally have an average particle size of less than about 50 microns (325 mesh, Standard U.S. Sieve Series). In most cases, the active ingredient will be present in dust formulations at a concentration in the range of 1 to 15%, and occasionally from 1% to about 30%, the balance of the composition typically comprising one or more agriculturally acceptable inerts as adjuvant, carrier, or diluent.

The nematicidal compounds of the invention may also be formulated as wettable powders. These formulations are in the form of finely divided particles which disperse readily in water or other liquid vehicles. The wettable powder is ultimately applied as a dry dust or a dispersion in water or other liquid. Typical carriers for wettable powders include fuller's earth, kaolin clays, silicas, and other highly absorbent or adsorbent inorganic diluents. The concentration of active ingredient in wettable powders is dependent upon physical properties of the active ingredient and the absorbency of the carriers. Liquids and low melting solids (mp less than 100° C.) are suitably formulated in the concentration range of 5 to 50% by weight; usually 10 to 30%; high melting solids (mp greater than 100° C.) being formulated in the range of 5 to 95% by weight, usually 50 to 85%. An agriculturally acceptable carrier or diluent, frequently including a small amount of a surfactant to facilitate wetting, dispersion and suspension, accounts for the balance of the formulation.

Microencapsulated or other controlled release formulations may also be used for application of compounds in accordance with this invention.

Emulsifiable concentrates (EC's) are homogeneous liquid compositions, usually containing the active ingredient dissolved in a liquid carrier. Commonly used liquid carriers include xylene, heavy aromatic naphthas, isophorone, and other nonvolatile or slightly volatile organic solvents. For application of the nematicide, these concentrates are dispersed in water, or other liquid vehicle, forming an emulsion, and are normally applied as a spray to the area to be treated. The concentration of the essential active ingredient in EC's may vary according to the manner in which the composition is to be applied, but, in general, is in the range of 0.5 to 95%, frequently 10 to 80%, by weight of active ingredient, with the remaining 99.5% to 5% being surfactant and liquid carrier.

Flowables are similar to EC's except that the ingredient is suspended in a liquid carrier, generally water. Flowables, like EC's, may include a small amount of a surfactant, and contain active ingredient in the range of 0.5 to 95%, frequently from 10 to 50%, by weight of the composition. For application, flowables may be diluted in water or other liquid vehicle, and are normally applied as a spray to the area to be treated.

Typical wetting, dispersing or emulsifying agents used in these formulations include, but are not limited to, the alkyl and alkylaryl sulfonates and sulfates and their sodium or calcium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; addition products of longchain mercaptans and ethylene oxide; and addition products of alkylphenols such as nonylphenol and ethylene oxide. Many other types of useful surface-active agents are available in commerce. The surface-active agent, when used, normally comprises from 1 to 15% by weight, of the nematicidal composition.

Other useful formulations include simple solutions of the active ingredient in a relatively non-volatile solvent such as corn oil, kerosene, propylene glycol, or other organic solvents. This type of formulation is particularly useful for ultra-low volume application.

The concentration of active ingredient in use dilution is normally in the range of about 2% to about 0.1%. Many variations of spraying, dusting, and controlled or slow release compositions in the art may be used by substituting or adding a compound of this invention to compositions known or apparent to the art.

The compositions may be formulated and applied with other suitable active ingredients, including other nematicides, insecticides, acaricides, fungicides, plant regulators, herbicides, fertilizers, etc.

In applying the foregoing chemicals, an effective nematode controlling amount of active ingredient must be applied, sometimes referred to herein as a "nematicidal amount." While the application rate will vary widely depending on the choice of compound, the formulation and mode of application, the plant species being protected and the planting density, a suitable use rate may be in the range of 0.5 to 25 kg/hectare, preferably 1 to about 20 kg/hectare.

The compounds of this invention are usually applied by incorporating a formulation thereof into the soil in which plants or agricultural crops are or are to be planted, i.e., the locus of infestation. This may be achieved by incorporating the compounds into the soil or by broadcasting the formulation over the planted area or the area to be planted or by limiting the application to a small area or band in the root zone where plants are or are to be planted. It will be readily apparent where the latter method is employed that a nematicidal amount, that is, a nematicidal concentration in the soil, must be applied to the root zone. A suitable concentration for this purpose is in the range of 0.1 to about 50 parts by weight of compound of the invention per million parts of soil.

However, in a significant aspect of the invention, it has been found that certain of the polyhaloalkene derivatives of the invention have efficacy against nematodes by foliar application, i.e., the compounds are systemic nematicides. This aspect is exemplified hereinafter.

The following are specific examples of formulations which may be utilized in accordance with the present invention. In these formulations the precentages are wt/wt.

1. Typical dust formulation:

| | |
|---|---|
| Test Compound | 5% |
| Base | 95% |

-continued

| | |
|---|---|
| 96% | Attaclay |
| 2% | highly purified sodium lignosulfonate (100%) |
| 2% | powered sodium alkylnapthalene sulfonate (75%) |

2. Typical emulsifiable-concentrates:

| (A) | Test Compound | 5.0% |
|---|---|---|
| | Emulsifier A | 4.0% |
| | Emulsifier B | 0.4% |
| | Emulsifier C | 0.8% |
| | Emulsifier D | 1.3% |
| | Refined xylene solvent | 88.5% |

Emulsifier A is the anionic calcium salt of dodecylbenzene sulfonate. Emulsifier B is a nonionic 6-molar ethylene oxide condensation product of nonylphenol. Emulsifier C is a nonionic 30-molar ethylene oxide condensation product of nonylphenol. Emulsifier D is a nonionic paste of 100% polyalkylene glycol other.

| (B) | Test compound | 21.3% |
|---|---|---|
| | Emulsifier A | 4.2% |
| | Emulsifier B | 0.5% |
| | Emulsifier C | 0.9% |
| | Emulsifier D | 1.4% |
| | Refined xylene solvent | 71.7% |
| (C) | Test compound | 5.0% |
| | Emulsifier E | 4.0% |
| | Emulsifier F | 3.0% |
| | Emulsifier G | 3.0% |
| | Dormant spray oil solvent (non-volatile) | 85.0% |

Emulsifier E is an oil-soluble nonionic blend of polyoxyethylene ethers commerically available under the trademark and designation "T Mulz 808A". Emulsifier F is a formulated nonionic concentrate commerically available under the trademark and designation "FloMo 200-4". Emulsifier G is the anionic free acid of a complex organic phosphate ester commerically available under the trademark and designation "Gafac RE-410".

3. Typical granule formulations:

| (A) | Test compound (technical) | 5.0% |
|---|---|---|
| | Attapulgite carrier/diluent | 95.0% |

The carrier/diluent is a 20/40 or 60/90 mesh hydrated aluminum magnesium silicate of low volatile matter having 2% free moisture.

| (B) | Test compound (technical) | 5.0% |
|---|---|---|
| | Ground corn cobs, 14/40 mesh | 95.0% |
| (C) | Test compound (as emulsifiable concentrate 2(B) above) | 23.5 |
| | Attapulgite carrier/diluent [3(A) above] | 76.5% |

4. Typical solution formulation:

| | | |
|---|---|---|
| | Test compound | 0.3% |
| | Acetone | 55.9% |
| | Water | 43.8% |

Biological Testing

Compounds of this invention were tested as follows for nematicidal and anthelmintic activity as dust formulations (initial and residual activity) and as acetone/water formulations (systemic activity). The formulations are described above.

1. Initial Root-Knot Nematicidal Activity

The activity against root-knot nematode (*Meloidogyne incognita*) was determined by incorporating the compound of the invention in nematode infested soil at rates in the range of 10 ppm to 0.078 ppm of compound. Several tomato or cucumber seedlings were planted in the nematode infested soil. Two weeks after planting the test pots were evaluated to ascertain the degree of galling (swelling) on the roots of the plants, indicating the control provided by the test chemical.

The results expressed as precent control (determined by knot index) are set forth as averages in Table 2 (appended). Knot index is a numerical designation assigned at evaluation, having the following meanings:

| Knot Index | Observations |
|---|---|
| 0 | No swellings - complete control |
| 1 | 75% less swellings than control plants |
| 2 | 50% less swellings than control plants |
| 3 | 25% less swellings than control plants |
| 4 | About same as control plants - no control. |

Percent control is related to knot index as follows:

| Knot Index | Percent Control |
|---|---|
| 0 | 100 |
| 1 | 75 |
| 2 | 50 |
| 3 | 25 |
| 4 | 0 |

When the Knot Index is between 0 and 1 it is further subdivided as follows to indicate how close the percent control is to 75% or 100%:

| Knot Index | Percent Control |
|---|---|
| 0.8 | 80 |
| 0.5 | 90 |
| 0.1–0.4 | 95–99 |

The results demonstrate that compounds of this invention are highly effective against root-knot nematodes at the application rates tested.

2. Residual Root-Knot Nematicidal Activity

The ability of nematicidal compounds of the invention to control root-knot nematode infestations in soil over a period of time after treatment was evaluated. Dust formulations of test compound (5%) were incorporated into soil samples at test compound rates of 5 and 10 ppm. Subsequently, the treated soil samples were inoculated with nematode inoculum at weekly intervals, and Knot Index and Percent Control determined on seedlings planted in the soil samples. Specifically, soil treated with test compound was placed in 7.6 cm diameter fiber pots and stored in a greenhouse. At one, two and four weeks post-treatment, the appropriate number of pots was infested with root-knot nematode eggs and larvae. A cucumber or tomato seedling was planted in each pot and evaluated approximately two weeks after the soil infestation to obtain the test results reported in Tables 3 and 3a appended. The data shows that as compared with untreated, but nematode-inoculated control soil, planted with seedlings (which showed no nematode control), substantial residual activity was exhibited with most of the test compounds at the application rates tested.

3. Stunt Nematode Test

The procedure was substantially the same as in the initial root-knot nematode tests described above except that rates of application of formulated compound were 2.5 and 5 ppm in soil containing a corn seedling, with subsequent inoculation of the soil with combined larvae and adult stunt nematodes. The samples were evaulated approximately four weeks after infestation. The results (Tables 4 and 4a appended) indicate good control at the test application rates as compared with untreated samples where no control was observed. "Percent control" means the difference between average population counts between untreated and treated samples, divided by average population count of untreated sample, multiplied by 100.

4. Lesion Nematode Test

The procedure was substantially the same as in the stunt nematode test described above except that pea seedlings were used. The results (Table 5 appended) show good control with many of the compounds at the application rates tested as compared with untreated samples (no control). "Percent Control" is defined as follows:

$$\left[ \frac{\frac{\text{Population Count in Check}}{\text{Wt of Roots in Check Plant}} - \frac{\text{Population Count in Trtmt}}{\text{Wt of Roots in Treated Plants}}}{\frac{\text{Population Count in Check}}{\text{Wt of Roots in Check Plant}}} \right] \times 100$$

5. Cyst Nematode Test

The procedures was substantially the same as described in the stunt nematode test except soybean seedlings were used. "Percent Control" (Table 6 appended) is as defined in the stunt nematode test results. The data indicate good control by most of the compounds at the application rates tested.

6. Soil Mobility

The ability of nematicidal compounds of the invention to move through nematode-infested soil and to control the nematodes was evaluated by incorporating 5% dust formulations of test compound at 30 ppm rates into pots of root-knot nematode infested soil, and subsequently eluting the soil with 15 cm of water (equivalent to 15 cm of rainfall) into a series of two or more pots of untreated, but nematode-infested, soil. Specifically, the pots were 8 cm diameter plastic pots containing a 10 $cm^3$ layer of sand over a coarse grade filter paper disc. Sufficient soil was placed over the sand to fill the pots, and a second filter paper disc was placed over the soil. Each test compound-treated pot was nested over a series of two or more pots containing untreated, but nematode-infested soil, also containing sand filter paper discs as described for the treated soil pots. Fifteen cm of water was slowly dripped into the top pots and the pots were allowed to drain for 16–18 hours to remove excess water. The top filter of each pot was then removed and the pots were planted with a cucumber or tomato seedling. The seedlings were evaluated approximately two weeks after planting to give the test results reported in Tables 7 and 7a appended. The data indicate good soil mobility and nematicide control at the application rates tested as compared to untreated systems which showed no nematode control. "Knot Index" and "Percent Control" are as defined in the initial root-knot nematode tests above.

8. Systemic Activity

Compounds of the invention were tested for basipetal systemic activity against the root-knot nematode. In this test, tomato plants are grown in 10.2 cm diameter fiber pots containing steam-pasteurized soil mix (50%, soil, 50% sand) until 4–6 true leaves appear. Three of the pots are then placed on a turntable in a spray hood and the plants sprayed with 50 ml of water/acetone solution containing the test compound. The soil surface is covered during the spraying to prevent spraying of the soil. After treatment, the potted plants are placed in a lighted drying chamber. The plants are then grown in a growth chamber at 25° C. for three days and inoculated with a standard nematode culture by incorporating the inoculum into the top cm of soil in the pots. The plants are returned to the growth chamber for about two weeks at which time the pots are allowed to dry until the plants begin to wilt. The roots are shaken free of soil and the degree of galling (swelling) noted as compared to galling of untreated control plants. The results are expressed as Knot Index and Percent Control as defined in the initial root-knot nematode activity tests reported above in Table 2. Table 8 appended reports the test results. The data indicate that many of the compounds exhibited good systemic nematicidal activity at the application rates tested as compared with untreated plants wherein no nematicidal activity was evident. Systemic nematicidal activity of any substantial degree is highly unusual and desirable and is not available from any commerical nematicides.

9. C. Elegans Nematode Screening Test and Evaluation

This in-vitro test using the free-living nematode Caenorhabditis elegans, is a modification of the assay developed by Simpkin and Coles, J. Chem. Tech. Tiotechnol, 31:66–69 (1981). In this test, nematicidal activity is evaluated by placing a suspension of C. elegans nemalodes in a medium containing a food source (E. coli) and a candidate nematicide at test rates of 5.0–0.156 ppm. One milliliter of a test medium consisting of 5 mg ampicillin, 10,000 units of mycostatin and 10 ml of a dense suspension of Escherichia coli per 100 ml of a buffer solution, was pipetted into each well of a 24-well microtiter plate. The candidate nematicide, suspended at the appropriate concentration in dimethylsulfoxide, was added to the wells in 2.5 µm volumes. Each rate of application was replicated two to three times. After thorough mixing of the contents of each well, 50 to 100 µl of a nematode suspension in a buffer was added so that each well received 10–15 nematodes. After the nematodes were added, the microtiter plates were incubated at 20° C. for 5–6 days.

The effect of the candidate nematicide on the survival and the reproduction of C. elegans was then evaluated by comparison of the level of population developed in the treated wells with that in untreated wells. Specific effects on population development, such as reduced egg hatch or molting disruption, were noted if they were evident. Tables 9 and 10 appended show high activity test results for many compounds of the invention at the application rates tested.
TABLE 1
$$F_2C=\underset{\underset{F}{|}}{C}-CH_2CH_2X-R$$
| Cmpd. No. | X | R | Empirical Formula |
|---|---|---|---|
| 1 | S | 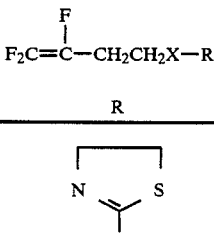 | $C_7H_8F_3NS_2$ |
| 2 | S | 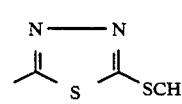 | $C_7H_7F_3N_2S_3$ |
| 3 | O | C(O)CF$_2$CF$_2$CF$_3$ | $C_8H_4F_{10}O_2$ |
| 4 | O | 4-chlorobenzoyl | $C_{11}H_8ClF_3O_2$ |
| 5 | N | 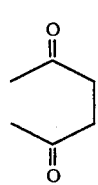 | $C_8H_8F_3NO_2$ |
| 6 | N | =C=S | $C_5H_4F_3NS$ |
| 7 | CH$_2$ | OH | $C_5H_7F_3O$ |
| 8 | S | 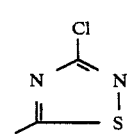 | $C_6H_4ClF_3N_2S_2$ |
| 9 | S | 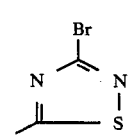 | $C_6H_4BrF_3N_2S_2$ |
| 10 | S | 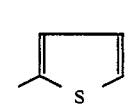 | $C_8H_7F_3S_2$ |
| 11 | S | 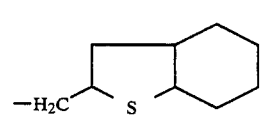 | $C_{13}H_{11}F_3S_2$ |
| 12 | S | 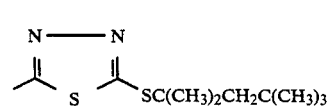 | $C_{14}H_{21}F_3N_2S_3$ |
| 13 | S | 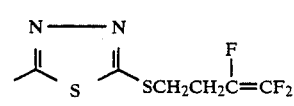 | $C_{10}H_{18}F_6N_2S_3$ |
| 14 | S | 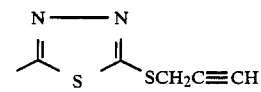 | $C_9H_7F_3N_2S_3$ |

TABLE 1-continued $$F_2C\!=\!\underset{\underset{F}{|}}{C}\!-\!CH_2CH_2X\!-\!R$$

| Cmpd. No. | X | R | Empirical Formula |
|---|---|---|---|
| 15 | S | (N=N heterocycle with S, isopropylidene, SCH₂-cyclopropyl) | $C_9H_9F_3N_2S_3$ |
| 16 | S | (N=N heterocycle with O, isopropylidene, phenyl (φ)) | $C_{12}H_9F_3N_2OS$ |
| 17 | S | (N=N heterocycle with O, isopropylidene, 4-chlorophenyl) | $C_{12}H_8ClF_3N_2OS$ |
| 18 | S | $-CH_2CO_2CH_2CH_2C(F)\!=\!CF_2$ | $C_{10}H_{10}F_6O_2S$ |
| 19 | O | $-C(O)CF_2CF_3\cdot(CH_3CH_2)_2O$ | $C_{11}H_{14}F_8O_3$ |
| 20 | O | $-C(O)$-(thiophene with NO₂) | $C_9H_6F_3NO_5$ |
| 21 | O | $-C(O)$-(furan with NO₂) | $C_9H_6F_3NO_5$ |
| 22 | O | $-C(O)$-(pyrrole, NH) | $C_9H_7F_3NO_2$ |
| 23 | O | $-C(O)CH_2S-$(thiazoline) | $C_9H_{10}F_3NO_2S_2$ |
| 24 | N | (methyl, ethylphenyl, SO₂) | $C_{11}H_8F_3NO_3S$ |

TABLE 1a $$\underset{\underset{F}{|}}{\overset{F}{|}}C\!=\!\overset{F}{\underset{|}{C}}(CH_2)_2SR \text{ wherein:}$$

R is 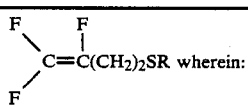

| Compound No. | $R^2$ | Empirical Formula M.P. (°C.) |
|---|---|---|
| 25 | $-CH_2CH_2CF\!=\!CF_2$ | $C_{10}H_8F_6N_2S_3$ liquid |
| 26 | 4-nitrophenylmethyl | $C_{13}H_{10}F_3N_3O_2S_3$ liquid |

R is 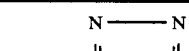

| Compound No. | $R^3$ | Empirical Formula M.P. (°C.) |
|---|---|---|
| 27 | $-SCH_2CH_2F$ | $C_8H_8F_4N_2S_3$ liquid |
| 28 | $-SCH_2CH_2C\!\equiv\!N$ | $C_9H_8F_3N_3S_3$ liquid |
| 29 | $-SC_3H_7$ | $C_9H_{11}F_3N_2S_3$ |

TABLE 1a-continued

| | | |
|---|---|---|
| 30 | —SCH(CH3)2 | C9H11F3N2S3 liquid |
| 31 | —SCH2CH=CH2 | C9H9F3N2S3 liquid |
| 32 | —SCH2φ | C13H11F3N2S3 liquid |
| 33 | —SCH2φ, 4-bromo | C13H10BrF3N2S3 S (49–51) |
| 34 | —SCH2φ, 2-fluoro | C13H10F4N2S3 liquid |
| 35 | —SCH2φ, 4-nitro | C13H10F3N3O2S3 liquid |
| 36 | 2-thienylmethylthio | C11H9F3N2S4 liquid |
| 37 | -φ, 4-chloro | C12H8ClF3N2S2 S (68–69) |

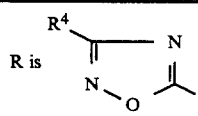

R is

| Compound No. | R4 | Empirical Formula M.P. (°C.) |
|---|---|---|
| 38 | —CH2φ, 4-fluoro | C13H10F4N2OS liquid |
| 39 | -φ, 4-chloro | C12H8ClF3N2OS S (49–52) |
| 40 | -φ, 4-nitro | C12H8F3N3O3S S (61–64) |

R is $$\underset{R^5}{\overset{N\text{---}N}{\diagdown\!\!\diagup}}_O$$

| Compound No. | R5 | Empirical Formula M.P. (°C.) |
|---|---|---|
| 41 | —C3H7 | C9H11F3N2OS liquid |
| 42 | —CH2φ | C13H11F3N2OS liquid |
| 43 | —CH2φ, 4-chloro | C13H10ClF3N2OS liquid |
| 44 | —CH2φ, 2-fluoro | C13H10F4N2OS liquid |
| 45 | —CH2φ, 4-fluoro | C13H10F4N2OS liquid |
| 46 | —CH2φ, 2,4-difluoro | C13H9F5N2OS liquid |
| 47 | —CH2CH2φ | C14H13F3N2OS liquid |
| 48 | —φ, 3-chloro | C12H8ClF3N2OS S (55) |
| 49 | —φ, 4-bromo | C12H8BrF3N2OS S (58–61) |
| 50 | —φ, 4-fluoro | C12H8F4N2OS S (56–59) |

TABLE 1b

| Cmpd. No. | Name |
|---|---|
| 1 | 2-(3,4,4-trifluoro-3-butenylthio)-4,5-dihydrothiazole |
| 2 | 2-methylthio-5-(3,4,4-trifluoro-3-butenylthio)-1,3,4-thiadiazole |
| 3 | (3,4,4-trifluoro-3-butenyl) heptafluorobutyrate |
| 4 | (3,4,4-trifluoro-3-butenyl) 4-chlorobenzoate |
| 5 | N-(3,4,4-trifluoro-3-butenyl)succinimide |
| 6 | (3,4,4-trifluoro-3-butenyl) isothiocyanate |
| 7 | 4,5,5-trifluoro-4-penten-1-ol |
| 8 | 3-chloro-5-(3,4,4-trifluoro-3-butenylthio)-1,2,4-thiadiazole |
| 9 | 3-bromo-5-(3,4,4-trifluoro-3-butenylthio)-1,2,4-thiadiazole |
| 10 | 2-(3,4,4-trifluoro-3-butenylthio)thiopene |

TABLE 1b-continued

| Cmpd. No. | Name |
|---|---|
| 11 | 2-(3,4,4-trifluoro-3-butenylthiomethyl)-thianaphthene |
| 12 | 2-(1,1,3,3-tetramethylbutylthio)-5-(3,4,4-trifluoro-3-butenylthio)-1,3,4-thiadiazole |
| 13 | 2,5-di(3,4,4-trifluoro-3-butenylthio)-1,3,4-thiadiazole |
| 14 | 2-propargylthio-5-(3,4,4-trifluoro-3-butenylthio)-1,3,4-thiadiazole |
| 15 | 2-cyclopropylmethylthio-5-(3,4,4-trifluoro-3-butenylthio)-1,3,4-thiadiazole |
| 16 | 2-phenyl-5-(3,4,4-trifluoro-3-butenylthio)-1,3,4-oxadiazole |
| 17 | 2-(4-chlorophenyl)-5-(3,4,4-trifluoro-3-butenylthio)-1,3,4-oxadiazole |
| 18 | (3,4,4-trifluoro-3-butenyl) (3,4,4-trifluoro-3-butenylthio)acetate |
| 19 | (3,4,4-trifluoro-3-butenyl) pentafluoropropionate, mono diethyl etherate |
| 20 | (3,4,4-trifluoro-3-butenyl) 2-thiophenecarboxylate |
| 21 | (3,4,4-trifluoro-3-butenyl) 5-nitro-2-furancarboxylate |
| 22 | (3,4,4-trifluoro-3-butenyl) 2-pyrrolecarboxylate |
| 23 | (3,4,4-trifluoro-3-butenyl) [2-(4,5-dihydrothiazolyl)thio]acetate |
| 24 | N-(3,4,4-trifluoro-3-butenyl)saccharine |
| 25 | 3,5-di(3,4,4-trifluoro-3-butenylthio)-1,2,4-thiadiazole |
| 26 | 3-(4-nitrophenylmethylthio)-5-(3,4,4-trifluoro-3-butenylthio)-1,2,4-thiadiazole |
| 27 | 2-(2-fluoroethylthio)-5-(3,4,4-trifluoro-3-butenylthio)-1,3,4-thiadiazole |
| 28 | 2-(2-cyanoethylthio)-5-(3,4,4-trifluoro-3-butenylthio)-1,3,4-thiadiazole |
| 29 | 2-propylthio-5-(3,4,4-trifluoro-3-butenylthio)-1,3,4-thiadiazole |
| 30 | 2-(1-methylethylthio)-5-(3,4,4-trifluoro-3-butenylthio)-1,3,4-thiadiazole |
| 31 | 2-(2-propenylthio)-5-(3,4,4-trifluoro-3-butenylthio)-1,3,4-thiadiazole |
| 32 | 2-phenylmethylthio-5-(3,4,4-trifluoro-3-butenylthio)-1,3,4-thiadiazole |
| 33 | 2-(4-bromophenylmethylthio)-5-(3,4,4-trifluoro-3-butenylthio)-1,3,4-thiadiazole |
| 34 | 2-(2-fluorophenylmethylthio)-5-(3,4,4-trifluoro-3-butenylthio)-1,3,4-thiadiazole |
| 35 | 2-(4-nitrophenylmethylthio)-5-(3,4,4-trifluoro-3-butenylthio)-1,3,4-thiadiazole |
| 36 | 2-(2-thienylmethylthio)-5-(3,4,4-trifluoro-3-butenylthio)-1,3,4-thiadiazole |
| 37 | 2-(4-chlorophenyl)-5-(3,4,4-trifluoro-3-butenylthio)-1,3,4-thiadiazole |
| 38 | 3-(4-fluorophenylmethyl)-5-(3,4,4-trifluoro-3-butenylthio)-1,2,4-oxadiazole |
| 39 | 3-(4-chlorophenyl)-5-(3,4,4-trifluoro-3-butenylthio)-1,2,4-oxadiazole |
| 40 | 3-(4-nitrophenyl)-5-(3,4,4-trifluoro-3-butenylthio)-1,2,4-oxadiazole |
| 41 | 2-propyl-5-(3,4,4-trifluoro-3-butenylthio)-1,3,4-oxadiazole |
| 42 | 2-phenylmethyl-5-(3,4,4-trifluoro-3-butenylthio)-1,3,4-oxadiazole |
| 43 | 2-(4-chlorophenylmethyl)-5-(3,4,4-trifluoro-3-butenylthio)-1,3,4-oxadiazole |
| 44 | 2-(2-fluorophenylmethyl)-5-(3,4,4-trifluoro-3-butenylthio)-1,3,4-oxadiazole |
| 45 | 2-(4-fluorophenylmethyl)-5-(3,4,4-trifluoro-3-butenylthio)-1,3,4-oxadiazole |
| 46 | 2-(2,4-difluorophenylmethyl)-5-(3,4,4-trifluoro-3-butenylthio)-1,3,4-oxadiazole |
| 47 | 2-(2-phenylethyl)-5-(3,4,4-trifluoro-3-butenylthio)-1,3,4-oxadiazole |
| 48 | 2-(3-chlorophenyl)-5-(3,4,4-trifluoro-3-butenylthio)-1,3,4-oxadiazole |
| 49 | 2-(4-bromophenyl)-5-(3,4,4-trifluoro-3-butenylthio)-1,3,4-oxadiazole |
| 50 | 2-(4-fluorophenyl)-5-(3,4,4-trifluoro-3-butenylthio)-1,3,4-oxadiazole |

TABLE 1c
Substituted Thiadiazolyl/Oxadiazolyl Compounds

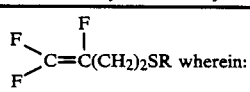

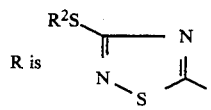

| Compound No. | R² | M.P. (°C.) |
|---|---|---|
| 51 | phenylmethyl- | liquid |
| 52 | 4-chlorophenylmethyl- | liquid |
| 53 | 4-chlorophenylthiomethyl- | liquid |
| 54 | R is (structure with I) | liquid |
| 55 | R is (structure with S-CH₂-C₆H₄-NO₂) | liquid |

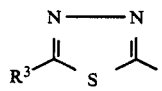

| Compound No. | R³ | M.P. (°C.) |
|---|---|---|
| 56 | 4-chlorophenylmethyl- | liquid |
| 57 | —SCH₂CH₃ | liquid |
| 58 | —SCH₂CF₃ | liquid |
| 59 | —SC₄H₉ | liquid |
| 60 | —SCH(CH₃)C₂H₅ | liquid |
| 61 | —SCH₂CH(CH₃)₂ | liquid |
| 62 | —S(CH₂)₂CClFCBrF₂ | liquid |
| 63 | —S(CH₂)₇CH₃ | liquid |
| 64 | —S(CH₂)₁₀CH₃ | liquid |
| 65 | —S(CH₂)₂CH=CH₂ | liquid |
| 66 | —SCH(CH₃)CH=CH₂ | liquid |
| 67 | —SCH₂C(CH₃)=CH₂ | liquid |
| 68 | —SCH₂CH=CHCH₃ | liquid |
| 69 | —S(CH₂)₃CH=CH₂ | liquid |
| 70 | —SCH₂CH=C(CH₃)₂ | liquid |
| 71 | —SCH₂C(Cl)=CH₂ | liquid |
| 72 | —SCH₂C(Br)=CH₂ | liquid |
| 73 | —SCH₂CH=C(Br)₂ | liquid |
| 74 | —S(CH₂)₂CH=C(Cl)—(cyclopropyl) | solid (55°) |
| 75 | —SCH₂C≡N | solid (60°) |
| 76 | —S(CH₂)₃C≡N | liquid |
| 77 | —S(CH₂)₄C≡N | liquid |
| 78 | —H₂C-(isoxazole with CH₃, CH₃) | liquid |
| 79 | 2,4-dimethylphenoxymethyl- | liquid |
| 80 | 3-chlorophenylmethylthio- | liquid |
| 81 | 4-chlorophenylmethylthio- | solid (38°) |
| 82 | 3,4-dichlorophenylmethylthio- | liquid |
| 83 | 2,6-dichlorophenylmethylthio- | liquid |
| 84 | 2-bromophenylmethylthio- | liquid |
| 85 | 3-bromophenylmethylthio- | liquid |
| 86 | 3,5-dibromophenylmethylthio- | liquid |
| 87 | 3-fluorophenylmethylthio- | liquid |

TABLE 1c-continued

Substituted Thiadiazolyl/Oxadiazolyl Compounds

| | | |
|---|---|---|
| 88 | 4-fluorophenylmethylthio- | liquid |
| 89 | 2,4-difluorophenylmethylthio- | liquid |
| 90 | 2,5-difluorophenylmethylthio- | liquid |
| 91 | 3,4-difluorophenylmethylthio- | liquid |
| 92 | 2,6-difluorophenylmethylthio- | liquid |
| 93 | 2,3,4,5,6-pentafluorophenylmethylthio- | liquid |
| 94 | 2-chloro-6-fluorophenylmethylthio- | liquid |
| 95 | 2-iodophenylmethylthio- | liquid |
| 96 | 2-methylphenylmethylthio- | liquid |
| 97 | 3-methylphenylmethylthio- | liquid |
| 98 | 2-trifluoromethylphenylmethylthio- | liquid |
| 99 | 3-trifluoromethylphenylmethylthio- | liquid |
| 100 | 4-trifluoromethylphenylmethylthio- | liquid |
| 101 | 3-methoxyphenylmethylthio- | liquid |
| 102 | 4-methoxyphenylmethylthio- | solid (42–44°) |
| 103 | 4-trifluoromethoxyphenylmethylthio- | liquid |
| 104 | 2-cyanophenylmethylthio- | liquid |
| 105 | 3-cyanophenylmethylthio- | liquid |
| 106 | 4-cyanophenylmethylthio- | solid (51–57°) |
| 107 | 2-nitrophenylmethylthio- | liquid |
| 108 | 3-nitrophenylmethylthio- | liquid |
| 109 | 2-chloro-4-nitrophenylmethylthio- | liquid |
| 110 | 4-chloro-2-nitrophenylmethylthio- | liquid |
| 111 | 2-fluoro-4-nitrophenylmethylthio- | liquid |
| 112 | 2-methyl-3-nitrophenylmethylthio- | liquid |
| 113 | 2-nitro-5-methylphenylmethylthio- | liquid |
| 114 | 2-methoxy-5-nitrophenylmethylthio- | liquid |
| 115 | 3,5-dinitrophenylmethylthio- | liquid |
| 116 | 4-phenylphenylmethylthio- | solid (62°) |
| 117 | 2-methyl-3-phenylphenylmethylthio- | solid |
| 118 | anthracine-9-ylmethylthio- | liquid |
| 119 | 5-chlorothien-2-ylmethylthio- | liquid |
| 120 | 2-methylthiazol-1-ylmethylthio- | liquid |
| 121 | 2,6-dichloropyridin-4-ylmethylthio- | liquid |
| 122 | 1,3-benzodioxol-5-ylmethylthio- | liquid |
| 123 | phenylthiomethylthio- | liquid |
| 124 | 1-phenylethylthio- | liquid |
| 125 | 2-(4-nitrophenyl)ethylthio- | liquid |
| 126 | 3-phenoxypropylthio- | liquid |
| 127 | —N[C(O)CF$_3$][C$_2$H$_5$] | liquid |
| 128 | —N[C(O)CH$_3$][CH$_3$] | liquid |
| 129 | —N[C(O)CH$_3$][4-trifluoromethylphenyl] | solid |
| 130 | 1,2-bis(4-chlorophenyl)urea- | solid |
| 131 | —N[C(O)CF$_3$][4-methoxyphenyl] | solid |
| 132 | 4-trifluoromethylphenylamino- | solid |
| 133 | 4-methoxyphenylamino- | solid |
| 134 | 4-chlorophenylamino- | solid |
| 135 | —N[C(O)−△(H$_3$C)(CH$_3$)−CH=CCl$_2$][CH$_3$] | liquid |
| 136 | 1-(4-trifluoromethylphenyl)-2-(4-chlorophenyl)urea- | solid |
| 137 | 1-methyl-2-(4-chlorophenyl)urea- | solid (141–2°) |
| 138 | —N[C(O)CH$_3$][4-chlorophenyl] | solid (84–85°) |
| 139 | —N[C(O)CH$_3$][4-fluorophenyl] | solid (96–97°) |
| 140 | —N[C(O)−△(H$_3$C)(CH$_3$)−CH=CCl$_2$][4-methoxyphenyl] | liquid |
| 141 | 4-nitrophenylamino- | solid |
| 142 | 1-ethyl-2-(4-chlorophenyl)urea- | solid |
| 143 | —N[C(O)CH$_3$][4-methoxyphenyl] | solid |
| 144 | 1-(4-fluorophenyl)-2-(4-chlorophenyl)-urea | solid |
| 145 | —NHC$_2$H$_5$ | solid |
| 146 | 4-fluorophenylamino- | solid |
| 147 | —N[CH$_3$][2,4-dichlorophenylmethylcarbonyl] | liquid |
| 148 | —N[C(O)−△(H$_3$C)(CH$_3$)−CH=CCl$_2$][C$_2$H$_5$] | liquid |

TABLE 1c-continued

Substituted Thiadiazolyl/Oxadiazolyl Compounds

| | | |
|---|---|---|
| 149 | 4-bromophenylamino- | solid |
| 150 | —N[C(O)—(cyclopropyl with H₃C, CH₃, CH=CCl₂)][4-trifluoromethylphenyl] | liquid |
| 151 | —N[C₂H₅][phenylmethoxycarbonyl] | solid |
| 152 | —N[C(O)CH₃][C₂H₅] | liquid |
| 153 | bromomethylthio- | liquid |
| 154 | —N[C(O)CH₃][4-bromophenyl] | solid |
| 155 | —N[C(O)—(cyclopropyl with H₃C, CH₃, CH=CCl₂)][4-nitrophenyl] | solid |
| 156 | —N[C(O)—(cyclopropyl with H₃C, CH₃, CH=CCl₂)][4-fluorophenyl] | liquid |
| 157 | —S(CH₂)₃CH₂Cl | semi-solid |
| 158 | —SCH₂Cl | liquid |
| 159 | —S(CH₂)₄Cl | liquid |
| 160 | —S(CH₂)₂CH₂Cl | liquid |
| 161 | —S(CH₂)₃CH₂Br | solid (67–69°) |

R is 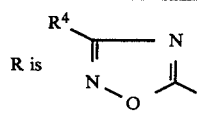

| Compound No. | R⁴ | M.P. (°C.) |
|---|---|---|
| 162 | 4-chlorophenylmethyl- | liquid |
| 163 | 4-methylphenyl- | liquid |
| 164 | phenylmethyl- | liquid |
| 165 | phenyl- | liquid |
| 166 | 2-chlorophenyl- | liquid |
| 167 | 3-chlorophenyl- | solid (48–51°) |
| 168 | 3-trifluoromethylphenyl- | solid (41–44°) |
| 169 | 4-methoxyphenylmethyl- | liquid |
| 170 | 3-nitrophenyl- | solid (69–71°) |

R is 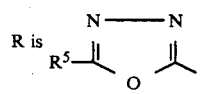

| Compound No. | R⁵ | M.P. (°C.) |
|---|---|---|
| 171 | —CH₃ | liquid |
| 172 | —C₂H₅ | liquid |
| 173 | —CH(CH₃)₂ | liquid |
| 174 | —CH₂CH(CH₃)₂ | liquid |
| 175 | —C(CH₃)₃ | liquid |
| 176 | —(CH₂)₄CH₃ | liquid |
| 177 | —(CH₂)₁₆CH₃ | solid (45°) |
| 178 | —C≡C(CH₂)₄CH₃ | liquid |
| 179 | —CH₂CH(CH₃)CF₃ | liquid |
| 180 | 2-chlorophenylmethyl- | liquid |
| 181 | 2-bromophenylmethyl- | liquid |
| 182 | 4-bromophenylmethyl- | solid (38–40°) |
| 183 | 2-methylphenylmethyl- | liquid |
| 184 | 3-methylphenylmethyl- | liquid |
| 185 | 2-bromo-4,5-dimethoxyphenylmethyl- | solid (54–59°) |
| 186 | 2-nitrophenylmethyl- | liquid |
| 187 | 4-nitrophenylmethyl- | liquid |
| 188 | thien-2-ylmethyl- | liquid |
| 189 | 1,4-benzodioxan-6-ylmethyl- | liquid |
| 190 | 1,3-benzodioxol-5-ylmethyl- | solid (69–71°) |

TABLE 1c-continued
Substituted Thiadiazolyl/Oxadiazolyl Compounds

| | | |
|---|---|---|
| 191 | 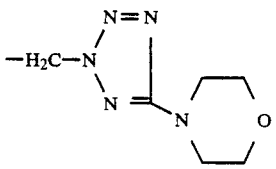 | liquid |
| 192 | 1-phenylethyl- | liquid |
| 193 | 2-(4-nitrophenyl)ethyl- | liquid |
| 194 | 2-(4-chlorophenyl)ethenyl- | liquid |
| 195 | 2-(4-bromophenyl)ethenyl- | liquid |
| 196 | 2-(2-fluorophenyl)ethenyl- | liquid |
| 197 | 3-phenylpropyl- | liquid |
| 198 | 4-phenylbutyl- | liquid |
| 199 | 4-chlorophenoxymethyl- | liquid |
| 200 | 4-methylphenoxymethyl- | liquid |
| 201 | 3-methyl-4-chlorophenoxymethyl- | liquid |
| 202 | 4-nitrophenoxymethyl- | liquid |
| 203 | 1-(4-chlorophenoxy)ethyl- | liquid |
| 204 | 1-(4-methylphenoxy)ethyl- | liquid |
| 205 | 2-(4-chlorophenylthio)ethyl- | solid (54–59°) |
| 206 | 1-(4-chlorophenoxy)propyl- | liquid |
| 207 | 2-chlorophenyl- | liquid |
| 208 | 2-bromophenyl- | liquid |
| 209 | 2,5-dichlorophenyl- | liquid |
| 210 | 4-(1-methylethyl)phenyl- | liquid |
| 211 | 2-methoxyphenyl- | liquid |
| 212 | 3-methoxyphenyl- | liquid |
| 213 | 4-methoxyphenyl- | liquid |
| 214 | 3,4-dimethoxyphenyl- | solid (51°) |
| 215 | 4-nitrophenyl- | solid (94–96°) |
| 216 | 2-aminophenyl- | solid (57–61°) |
| 217 | 4-hydroxyphenyl- | solid (96–101°) |
| 218 | 4-acetyloxyphenyl- | solid (63–66°) |
| 219 | 4-(methylaminocarbonyloxy)phenyl- | solid (108–111°) |
| 220 | 4-phenylphenyl- | solid (49–52°) |
| 221 | naphth-2-yl- | solid (70–72°) |
| 222 | naphth-1-yl- | solid (68°) |
| 223 | thien-2-yl- | liquid |
| 224 | furan-2-yl- | liquid |
| 225 | 4-methyl-1,2,3-thiadiazol-5-yl- | liquid |
| 226 | 2-(4-chlorophenyl)ethyl- | solid (43–45°) |
| 227 | 2-(2-chlorophenyl)ethyl- | liquid |
| 228 | 2-(4-fluorophenyl)ethyl- | liquid |
| 229 | phenylmethyl | liquid |

TABLE 2
Initial Activity Against the Root-knot Nematode

| Compound No. | Application Rate (ppm) | Percent Control |
|---|---|---|
| 1 | 10.0 | 100 |
| | 5.0 | 99 |
| | 2.5 | 99 |
| | 5.0 | 100 |
| | 2.5 | 100 |
| | 1.25 | 99 |
| | 0.625 | 100 |
| | 0.313 | 99 |
| | 0.625 | 100 |
| | 0.313 | 98 |
| | 0.156 | 95 |
| | 0.078 | 56 |
| 2 | 10.0 | 100 |
| | 5.0 | 96 |
| | 2.5 | 96 |
| | 5.0 | 99 |
| | 2.5 | 95 |
| | 1.25 | 86 |
| | 0.625 | 84 |
| | 0.313 | 38 |
| 3 | 10.0 | 95 |
| | 5.0 | 83 |
| | 2.5 | 71 |
| 4 | 2.5 | 99 |
| | 1.25 | 56 |
| | 0.625 | 44 |
| | 0.313 | 38 |
| 5 | 2.5 | 81 |
| | 1.25 | 70 |
| | 0.625 | 6 |
| | 0.313 | 0 |
| 6 | 10.0 | 100 |
| | 5.0 | 78 |
| | 2.5 | 38 |
| 7 | 10.0 | 79 |
| | 5.0 | 44 |
| | 2.5 | 25 |
| 8 | 2.5 | 100 |
| | 1.25 | 100 |
| | 0.625 | 100 |
| | 0.312 | 100 |
| | 0.625 | 100 |
| | 0.312 | 98 |
| | 0.156 | 95 |
| | 0.078 | 58 |
| 10 | 5.0 | 99 |
| | 2.5 | 95 |
| | 1.25 | 81 |
| | 0.625 | 63 |
| 11 | 5.0 | 83 |
| | 2.5 | 78 |
| | 1.25 | 67 |

TABLE 2-continued

Initial Activity Against the Root-knot Nematode

| Compound No. | Application Rate (ppm) | Percent Control |
|---|---|---|
|  | 0.625 | 0 |
| 12 | 2.5 | 100 |
|  | 1.25 | 79 |
|  | 0.625 | 69 |
|  | 0.313 | 8 |
| 13 | 2.5 | 99 |
|  | 1.25 | 99 |
|  | 0.625 | 96 |
|  | 0.313 | 71 |
|  | 0.625 | 95 |
|  | 0.313 | 79 |
|  | 0.156 | 13 |
|  | 0.078 | 0 |
| 14 | 2.5 | 83 |
|  | 1.25 | 25 |
|  | 0.625 | 0 |
|  | 0.313 | 0 |
| 15 | 2.5 | 100 |
|  | 1.25 | 97 |
|  | 0.625 | 31 |
|  | 0.313 | 6 |
| 16 | 2.5 | 95 |
|  | 1.25 | 44 |
|  | 0.625 | 25 |
|  | 0.313 | 0 |
| 17 | 10.0 | 100 |
|  | 5.0 | 100 |
|  | 2.5 | 100 |
| 18 | 10.0 | 100 |
|  | 5.0 | 99 |
|  | 2.5 | 96 |
|  | 5.0 | 80 |
|  | 2.5 | 69 |
|  | 1.25 | 38 |
|  | 0.625 | 19 |
|  | 0.313 | 0 |
| 19 | 10.0 | 69 |
|  | 5.0 | 75 |
|  | 2.5 | 58 |
| 20 | 2.5 | 98 |
|  | 1.25 | 63 |
|  | 0.625 | 6 |
|  | 0.313 | 0 |
| 21 | 2.5 | 64 |
|  | 1.25 | 31 |
|  | 0.625 | 8 |
|  | 0.313 | 0 |
| 22 | 2.5 | 96 |
|  | 1.25 | 44 |
|  | 0.625 | 0 |
|  | 0.313 | 0 |
| 23 | 10.0 | 96 |
|  | 5.0 | 84 |
|  | 2.5 | 76 |
| 24 | 10.0 | 78 |
|  | 5.0 | 63 |
|  | 2.5 | 19 |
| 25 | 2.5 | 99 |
|  | 1.25 | 97 |
|  | .625 | 97 |
|  | .312 | 78 |
| 26 | 2.5 | 86 |
|  | 1.25 | 63 |
|  | .625 | 0 |
|  | .312 | 0 |
| 27 | 2.5 | 100 |
|  | 1.25 | 99 |
|  | .625 | 79 |
|  | .312 | 31 |
| 28 | 2.5 | 100 |
|  | 1.25 | 98 |
|  | .625 | 86 |
|  | .312 | 81 |
| 29 | 2.5 | 99 |
|  | 1.25 | 99 |
|  | .625 | 99 |
|  | .312 | 95 |
| 30 | 2.5 | 100 |
|  | 1.25 | 99 |
|  | .625 | 99 |
|  | .312 | 97 |
| 31 | 2.5 | 99 |
|  | 1.25 | 96 |
|  | .625 | 78 |
|  | .312 | 69 |
|  | .625 | 63 |
|  | .312 | 44 |
|  | .156 | 13 |
|  | .078 | 0 |
| 32 | 2.5 | 100 |
|  | 1.25 | 99 |
|  | .625 | 97 |
|  | .312 | 78 |
|  | .625 | 98 |
|  | .312 | 69 |
|  | .156 | 31 |
|  | .078 | 8 |
| 33 | 2.5 | 97 |
|  | 1.25 | 84 |
|  | .625 | 70 |
|  | .312 | 38 |
| 34 | 2.5 | 100 |
|  | 1.25 | 99 |
|  | .625 | 99 |
|  | .312 | 86 |
|  | .625 | 99 |
|  | .312 | 86 |
|  | .156 | 64 |
|  | .078 | 38 |
| 35 | 2.5 | 100 |
|  | 1.25 | 98 |
|  | .625 | 70 |
|  | .312 | 67 |
|  | .625 | 97 |
|  | .312 | 51 |
|  | .156 | 6 |
|  | .078 | 0 |
| 35 | 2.5 | 100 |
|  | 1.25 | 99 |
|  | .625 | 96 |
|  | .312 | 69 |
|  | .625 | 99 |
|  | .312 | 71 |
|  | .156 | 25 |
|  | .078 | 0 |
| 37 | .625 | 0 |
|  | .312 | 0 |
|  | .156 | 0 |
|  | .078 | 0 |
| 38 | 2.5 | 98 |
|  | 1.25 | 96 |
|  | .625 | 76 |
|  | .312 | 63 |
| 39 | 2.5 | 100 |
|  | 1.25 | 98 |
|  | .625 | 84 |
|  | .312 | 19 |
|  | 2.5 | 100 |
|  | 1.25 | 99 |
|  | .625 | 83 |
|  | .312 | 19 |
| 40 | 2.5 | 99 |
|  | 1.25 | 84 |
|  | .625 | 56 |
|  | .312 | 0 |
| 41 | 2.5 | 100 |
|  | 1.25 | 100 |
|  | .625 | 98 |
|  | .312 | 76 |
|  | .625 | 100 |
|  | .312 | 97 |
|  | .156 | 84 |
|  | .078 | 31 |
| 42 | 2.5 | 100 |
|  | 1.25 | 98 |
|  | .625 | 98 |

TABLE 2-continued

Initial Activity Against the Root-knot Nematode

| Compound No. | Application Rate (ppm) | Percent Control |
|---|---|---|
|  | .312 | 86 |
|  | .625 | 96 |
|  | .312 | 83 |
|  | .156 | 50 |
|  | .078 | 38 |
| 43 | .625 | 99 |
|  | .312 | 78 |
|  | .156 | 38 |
|  | .078 | 13 |
|  | .5 | 99 |
|  | 2.5 | 97 |
|  | 1.25 | 56 |
|  | .625 | 13 |
| 44 | 2.5 | 98 |
|  | 1.25 | 86 |
|  | .625 | 76 |
|  | .312 | 50 |
| 45 | 2.5 | 99 |
|  | 1.25 | 99 |
|  | .625 | 99 |
|  | .312 | 95 |
| 46 | 2.5 | 99 |
|  | 1.25 | 98 |
|  | .625 | 98 |
|  | .312 | 85 |
| 47 | 2.5 | 100 |
|  | 1.25 | 96 |
|  | .625 | 95 |
|  | .312 | 95 |
| 48 | 2.5 | 98 |
|  | 1.25 | 95 |
|  | .625 | 78 |
|  | .312 | 64 |
|  | .625 | 87 |
|  | .312 | 56 |
|  | .156 | 38 |
|  | .078 | 6 |
| 49 | 2.5 | 100 |
|  | 1.25 | 100 |
|  | .625 | 100 |
|  | .312 | 98 |
| 50 | 2.5 | 100 |
|  | 1.25 | 99 |
|  | .625 | 99 |
|  | .312 | 78 |

TABLE 3

Residual Activity Against the Root-knot Nematode

| Cmpd. No. | Application Rate (ppm) | Inoculation, Weeks After Treatment | Percent Control |
|---|---|---|---|
| 1 | 10 | 1 | 98 |
|  |  | 2 | 44 |
|  |  | 4 | 0 |
|  | 10 | 1 | 99 |
|  |  | 2 | 75 |
|  |  | 4 | 42 |
|  | 5 | 1 | 99 |
|  |  | 2 | 63 |
|  |  | 4 | 25 |
| 2 | 10 | 1 | 77 |
|  |  | 2 | 56 |
|  |  | 4 | 69 |
|  | 10 | 1 | 96 |
|  |  | 2 | 38 |
|  |  | 4 | 50 |
|  | 5 | 1 | 98 |
|  |  | 2 | 38 |
|  |  | 4 | 42 |
| 8 | 5 | 1 | — |
|  |  | 2 | — |
|  |  | 4 | 98 |
| 13 | 10 | 1 | 99 |
|  |  | 2 | 99 |
|  |  | 4 | 95 |
|  | 5 | 1 | 98 |

TABLE 3-continued

Residual Activity Against the Root-knot Nematode

| Cmpd. No. | Application Rate (ppm) | Inoculation, Weeks After Treatment | Percent Control |
|---|---|---|---|
|  |  | 2 | 98 |
|  |  | 4 | 75 |
| 18 | 10 | 1 | 0 |
|  |  | 2 | 0 |
|  |  | 4 | 0 |
| 21 | 5 | 1 | 13 |
|  |  | 2 | 8 |
|  |  | 4 | 0 |

TABLE 3a

Residual Activity Against The Root-Knot Nematode - 5% Dust - Application Rate: 5 ppm

| Compound No. | Inoculation Post-Treatment | Percent Control |
|---|---|---|
| 25 | 1 Week | 100 |
|  | 2 Weeks | 97 |
|  | 4 Weeks | 98 |
| 27 | 1 Week | 99 |
|  | 2 Weeks | 97 |
|  | 4 Weeks | 99 |
| 28 | 1 Week | 100 |
|  | 2 Weeks | 100 |
|  | 4 Weeks | 8 |
| 29 | 1 Week | 100 |
|  | 2 Weeks | 98 |
|  | 4 Weeks | 81 |
| 30 | 1 Week | 98 |
|  | 2 Weeks | 97 |
|  | 4 Weeks | 83 |
| 31 | 1 Week | 97 |
|  | 2 Weeks | 97 |
|  | 4 Weeks | 95 |
| 32 | 1 Week | 99 |
|  | 2 Weeks | 99 |
|  | 4 Weeks | 82 |
|  | 1 Week | 99 |
|  | 2 Weeks | 99 |
|  | 4 Weeks | 98 |
| 35 | 1 Week | 99 |
|  | 2 Weeks | 96 |
|  | 4 Weeks | 84 |
| 36 | 1 Week | 98 |
|  | 2 Weeks | 99 |
|  | 4 Weeks | 95 |
| 41 | 1 Week | 97 |
|  | 2 Weeks | 63 |
|  | 4 Weeks | 6 |
| 42 | 1 Week | 99 |
|  | 2 Weeks | 97 |
|  | 4 Weeks | 0 |
| 43 | 1 Week | 100 |
|  | 2 Weeks | 100 |
|  | 4 Weeks | 100 |
| 44 | 1 Week | 100 |
|  | 2 Weeks | 100 |
|  | 4 Weeks | 100 |
| 45 | 1 Week | 99 |
|  | 2 Weeks | 100 |
|  | 4 Weeks | 98 |
| 46 | 1 Week | 99 |
|  | 2 Weeks | 100 |
|  | 4 Weeks | 99 |
| 47 | 1 Week | 96 |
|  | 2 Weeks | 25 |
|  | 4 Weeks | 0 |
| 48 | 1 Week | 97 |
|  | 2 Weeks | 97 |
|  | 4 Weeks | 69 |

TABLE 4

Initial Activity Against the Stunt Nematode

| Compound. No. | Rate of Application (ppm) | Percent Control |
|---|---|---|
| 1 | 10 | 61 |
|   | 5 | 30 |
| 2 | 5 | 72 |
| 6 | 5 | 51 |

TABLE 4a

Initial Activity Against the Stunt Nematode
Application rate: 5 ppm

| Compound No. | Percent Control |
|---|---|
| 25 | 89 |
|    | 56 |
| 27 | 62 |
| 28 | 38 |
| 29 | 56 |
| 30 | 66 |
| 31 | 52 |
| 32 | 84 |
| 33 | 52 |
| 34 | 88 |
|    | 56 |
| 35 | 77 |
|    | 83 |
| 36 | 64 |
|    | 91 |
| 41 | 29 |
| 42 | 76* |
|    | 33 |
| 43 | 81 |
|    | 76 |
|    | 62 |
| 44 | 75 |
| 45 | 80* |
| 46 | 65* |
| 47 | 35 |
| 48 | 82 |
|    | 66 |
| 49 | 58 |
| 50 | 53 |

*Some phytotoxicity

TABLE 5

Initial Activity Against the Lesion Nematode

| Compound No. | Rate of Application (ppm) | Percent Control |
|---|---|---|
| 1 | 5 | 82 |
|   | 5 | 52 |
|   | 2.5 | 0 |
| 2 | 5 | 0 |
| 10 | 2.5 | 33 |
| 18 | 5 | 0 |
| 21 | 2.5 | 54 |
| 25 | 2.5 | 77 |
|    | 2.5 | 79 |
| 27 | 2.5 | 63 |
| 28 | 2.5 | 45 |
| 29 | 2.5 | 68 |
| 30 | 2.5 | 75 |
| 31 | 2.5 | 11 |
| 32 | 2.5 | 28 |
|    | 2.5 | 15 |
|    | 1.25 | 0 |
|    | .625 | 0 |
| 33 | 2.5 | 46 |
| 34 | 2.5 | 52 |
|    | 2.5 | 58 |
|    | 2.5 | 55 |
| 35 | 2.5 | 52 |
|    | 2.5 | 78 |
| 36 | 2.5 | 59 |
|    | 2.5 | 19 |
|    | 1.25 | 2 |
|    | .625 | 0 |
|    | 2.5 | 71 |
| 41 | 2.5 | 64 |
| 42 | 2.5 | 73 |
|    | 2.5 | 82 |
| 43 | 2.5 | 93 |
|    | 2.5 | 78 |
| 44 | 2.5 | 88 |
| 45 | 2.5 | 41 |
| 46 | 2.5 | 77 |
| 47 | 2.5 | 69 |
| 48 | 2.5 | 85 |
|    | 2.5 | 78 |

TABLE 6

Initial Activity Against the Cyst Nematode

| Compound No. | Rate of Application (ppm) | Percent Control |
|---|---|---|
| 1 | 5 | 94 |
|   | 5 | 79[1] |
| 2 | 5 | 70 |
| 8 | 5 | 92 |
| 18 | 5 | 8 |
| 21 | 2.5 | 33 |
| 25 | 5 | 83 |
| 27 | 5 | 57 |
| 31 | 5 | 7 |
| 32 | 5 | 16 |
|    | 5 | 78 |
| 35 | 5 | 0 |
| 36 | 5 | 37 |
| 41 | 5 | 0 |
| 42 | 5 | 30 |
| 44 | 5 | 59 |
| 48 | 5 | 86 |

[1]Whole cysts rather than homogenized cysts were used.

TABLE 7

Soil Mobility Evaluations Against Root-knot Nematode

| Cmpd No. | Application Rate (ppm) | Location of Test Container | Percent Control |
|---|---|---|---|
| 1 | 30 | Top | 97 |
|   |    | Middle | 95 |
|   |    | Bottom | 85 |
|   | 10 | 1 (Top) | 100 |
|   |    | 2 | 100 |
|   |    | 3 | 100 |
|   |    | 4 | 99 |
|   |    | 5 | 97 |
|   |    | 6 (Bottom) | 42 |
|   | 5 | Top | 100 |
|   |    | Middle | 98 |
|   |    | Bottom | 99 |
|   | 2.5 | Top | 100 |
|   |    | Middle | 100 |
|   |    | Bottom | 100 |
|   | 1.25 | Top | 100 |
|   |    | Middle | 99 |
|   |    | Bottom | 96 |
|   | 0.625 | Top | 97 |
|   |    | Middle | 98 |
|   |    | Bottom | 77 |
|   | 0.313 | Top | 77 |
|   |    | Middle | 75 |
|   |    | Bottom | 25 |
| 2 | 30 | Top | 42 |
|   |    | Middle | 33 |
|   |    | Bottom | 25 |
| 8 | 5 | Top | 100 |
|   |    | Middle | 100 |
|   |    | Bottom | 96 |
| 18 | 30 | Top | 33 |
|    |    | Middle | 25 |

TABLE 7-continued

Soil Mobility Evaluations Against Root-knot Nematode

| Cmpd No. | Application Rate (ppm) | Location of Test Container | Percent Control |
|---|---|---|---|
|  |  | Bottom | 25 |
| 21 | 30 | Top | 100 |
|  |  | Middle | 96 |
|  |  | Bottom | 99 |

TABLE 7a

Soil Mobility Evaluations Against The Root-Knot Nematode - 5% Dust; Application Rate: 5 ppm

| Compound No. | Location of Test Container | Percent Control |
|---|---|---|
| 25 | TOP | 100 |
|  | MIDDLE | 69 |
|  | BOTTOM | 8 |
| 27 | TOP | 99 |
|  | MIDDLE | 100 |
|  | BOTTOM | 100 |
| 28 | TOP | 68 |
|  | MIDDLE | 83 |
|  | BOTTOM | 68 |
| 29 | TOP | 98 |
|  | MIDDLE | 81 |
|  | BOTTOM | 50 |
| 30 | TOP | 99 |
|  | MIDDLE | 100 |
|  | BOTTOM | 17 |
| 31 | TOP | 98 |
|  | MIDDLE | 86 |
|  | BOTTOM | 50 |
| 32 | TOP | 99 |
|  | MIDDLE | 75 |
|  | BOTTOM | 25 |
| 34 | TOP | 98 |
|  | MIDDLE | 67 |
|  | BOTTOM | 8 |
| 35 | TOP | 99 |
|  | MIDDLE | 50 |
|  | BOTTOM | 0 |
| 36 | TOP | 97 |
|  | MIDDLE | 17 |
|  | BOTTOM | 0 |
| 38 | TOP | 0 |
|  | MIDDLE | 0 |
|  | BOTTOM | 0 |
| 41 | TOP | 97* |
|  | MIDDLE | 95* |
|  | BOTTOM | 8 |
| 42 | TOP | 100 |
|  | MIDDLE | 100 |
|  | BOTTOM | 100 |
| 43 | TOP | 99 |
|  | MIDDLE | 97 |
|  | BOTTOM | 81 |
| 44 | TOP | 100 |
|  | MIDDLE | 100 |
|  | BOTTOM | 96 |
| 45 | TOP | 98 |
|  | MIDDLE | 97 |
|  | BOTTOM | 83 |
| 46 | TOP | 96 |
|  | MIDDLE | 97 |
|  | BOTTOM | 78 |
| 47 | TOP | 98 |
|  | MIDDLE | 96 |
|  | BOTTOM | 58 |
| 48 | TOP | 50 |
|  | MIDDLE | 0 |
|  | BOTTOM | 0 |
|  | TOP | 96* |
|  | MIDDLE | 75 |
|  | BOTTOM | 42 |
| 49 | TOP | 99 |
|  | MIDDLE | 71 |
|  | BOTTOM | 8 |
| 50 | TOP | 98 |
|  | MIDDLE | 71 |

TABLE 7a-continued

Soil Mobility Evaluations Against The Root-Knot Nematode - 5% Dust; Application Rate: 5 ppm

| Compound No. | Location of Test Container | Percent Control |
|---|---|---|
|  | BOTTOM | 33 |

*Some phytotoxicity

TABLE 8

Systemic Activity Against the Root-knot Nematodes

| Cmpd. No. | Application Test Rate (ppm) | Percent Control |
|---|---|---|
| 12 | 2000 | 73, 99 |
|  | 1000 | 42, 95 |
| 13 | 2000 | 79 |
| 15 | 2000 | 83 |
| 16 | 2000 | 67 |
| 17 | 2000 | 42 |
| 31 | 2000 | 71 |
|  | 1250 | 0 |
| 32 | 2000 | 25 |
| 33 | 2500 | 17 |
| 35 | 2000 | 0 |
| 36 | 2000 | 97 |
|  | 1250 | 17 |
| 41 | 2000 | 17 |
| 48 | 2000 | 50 |
|  | 2500 | 33 |

TABLE 9

Screen Against C. Elegans - Rate: 5 ppm

| Compound No. | Percent Inhibition of Reproduction | Percent Mortality |
|---|---|---|
| 25 | 100 | 75 |
| 26 | 100 | 100 |
| 27 | 38 | 0 |
| 31 | 38 | 0 |
| 32 | 100 | 100 |
| 33 | 100 | 100 |
| 34 | 100 | 25 |
| 35 | 100 | 100 |
| 37 | 100 | 100 |
| 39 | 100 | 100 |
| 43 | 100 | 25 |
| 44 | 25 | 0 |
| 45 | 25 | 0 |
| 48 | 100 | 88 |

TABLE 10

Evaluations Against C. Elegans

| Compound No. | Rate (PPM) | Percent Inhibition of Reproduction | Percent Mortality |
|---|---|---|---|
| 25 | 5 | 100 | 100 |
|  | 2.5 | 58 | 0 |
|  | 1.25 | 17 | 0 |
| 26 | 5 | 100 | 100 |
|  | 2.5 | 100 | 100 |
|  | 1.25 | 100 | 100 |
| 32 | 5 | 100 | 8 |
|  | 2.5 | 42 | 0 |
|  | 1.25 | 25 | 0 |
| 33 | 5 | 100 | 100 |
|  | 2.5 | 100 | 100 |
|  | 1.25 | 100 | 100 |
| 34 | 5 | 100 | 100 |
|  | 2.5 | 100 | 100 |
|  | 1.25 | 0 | 0 |
| 35 | 5 | 100 | 100 |
|  | 2.5 | 100 | 100 |
|  | 1.25 | 100 | 100 |
| 37 | 5 | 100 | 100 |
|  | 2.5 | 100 | 100 |

TABLE 10-continued

Evaluations Against *C. Elegans*

| Compound No. | Rate (PPM) | Percent Inhibition of Reproduction | Percent Mortality |
|---|---|---|---|
|  | 1.25 | 100 | 100 |
| 39 | 5 | 100 | 100 |
|  | 5 | 100 | 100 |
|  | 2.5 | 100 | 100 |
|  | 2.5 | 100 | 100 |
|  | 1.25 | 100 | 67 |
|  | 1.25 | 100 | 58 |
| 40 | 5 | 100 | 100 |
|  | 2.5 | 100 | 100 |
|  | 1.25 | 100 | 100 |
| 43 | 5 | 100 | 83 |
|  | 2.5 | 100 | 67 |
|  | 1.25 | 42 | 0 |
| 48 | 5 | 100 | 100 |
|  | 2.5 | 25 | 0 |
|  | 1.25 | 17 | 0 |

We claim:

1. Polyhaloalkene compounds of the formula: wherein X is sulfur, oxygen, or nitrogen, $Y^1$ and $Y^2$ are fluorine, Z is hydrogen or the same as $Y^1$ and $Y^2$, and n is 1–4; provided that:

(A) when X is sulfur, Z is fluorine and R is thienyl or substituted thienyl, thianaphthyl or substituted thianaphthyl, thiazolinyl or substituted thiazolinyl, oxadiazolyl or substituted oxadiazolyl, 3, 4, 4-trifluoro-3-butenyloxycarbonylmethyl, thiadiazolyl substituted by halogen or $R^2S$, wherein $R^2$ is 3,4,4-trifluoro-3-butenyl or $R^2$ is phenylmethyl or phenylthiomethyl each optionally substituted by halogen or nitro, wherein the thienyl, thianaphthyl, thiazolinyl and oxadiazolyl substituents are selected from aliphatic, aromatic and heterocyclic groups, halo, nitro, cyano, alkoxy, alkylthio, haloalkyl, haloalkoxy, halo-, nitro-, cyano-, alkoxy-, methylthio-, methylsulfinyl-, methylsulfoxy-, dimethylamino-, or phenoxy- substituted phenyl, polyhaloalkenylthio, phenylalkylthio, phenylthioalkylthio, propargylthio, and cycloalkylmethylthio; or R is thiadiazolyl substituted by $R^3$, wherein $R^3$ is substituted aryl, arylalkyl, aryloxyalkyl, alkylthio, haloalkylthio, haloarylthio, cyanoalkylthio, arylalkylthio, aryloxyalkylthio, arylthioalkylthio, heterocycloalkylthio, alkenylthio, haloalkenylthio, halocycloalkylalkenylthio, wherein said aryl or heterocyclo-substituents of $R^3$ may be mono-, di-, tri, tetra-, or penta-substituted, wherein said substituents are selected from methylthio, methylsulfinyl, methylsulfoxy, dimethylamino, phenoxy, halo, haloalkyl, alkoxy, haloalkoxy, cyano, nitro, and phenyl, or $R^3$ is an amino group mono- or di- substituted with members independently selected from alkyl, alkylcarbonyl, haloalkylcarbonyl, aryl, arylaminocarbonyl, arylalkylcarbonyl, arylalkoxycarbonyl, and 3-(2,2-dichloroethenyl)-2,2-dimethylcyclopropanecarbonyl;

(B) when X is oxygen, Z is fluorine and R is $C(O)R^1$, wherein $R^1$ is perfluoralkyl, phenyl or substituted phenyl, thienyl or substituted thienyl, furanyl or substituted furanyl, pyrollyl or substituted pyrollyl, or dihydrothiazolylthiomethyl, wherein the phenyl, thienyl, furanyl, pyrollyl substituents are selected from aliphatic, aromatic and heterocyclic groups, halo, nitro, cyano, alkoxy, alkylthio, haloalkyl, haloalkoxy, halo-, nitro-, cyano- or alkoxy-substituted phenyl, polyhaloalkenylthio, phenylalkylthio, phenylthioalkylthio, propargylthio, and cycloalkylmethylthio; and (C) when X is nitrogen, R taken with the nitrogen is an isothiocyanate, succinimide, or saccharine group; wherein the heterocyclo substituents of (A) and (B) are selected from thienyl, isoxazolyl, pyridinyl, thiazolyl, thiazolinyl, benzodioxanyl, benzodioxolyl, tetrazolyl, and furanyl.

2. Compounds of the formula of claim 1 wherein X is sulfur.

3. Compounds of the formula of claim 1 wherein X is sulfur and R is a substituted thiadiazolyl, or an oxadiazolyl group, substituted on a nuclear carbon atom.

4. Substituted thiadiazolyl compounds of claim 3 wherein the substituent is iodo.

5. Substituted oxadiazolyl compounds of claim 3 wherein the substituent is ($R^4$) wherein $R^4$ is halo, or optionally substituted aryl, or an arylalkyl group substituted with chloro, fluoro, alkyl, haloalkyl, alkoxy or nitro.

6. Substituted oxadiazolyl compounds of claim 3 wherein the substituent is ($R^5$), wherein $R^5$ is halo, or alkyl, haloalkyl, optionally substituted aryl, arylalkyl, aryloxyalkyl, arylthioalkyl, optionally substituted heterocycloalkyl, arylalkenyl or alkynyl.

7. Compounds of claim 2 selected from
2-(3,4,4-trifluoro-3-butenylthio)thiophene,
2-(3,4,4-trifluoro-3-butenylthio)-4,5-dihydrothiazole,
2-methylthio-5-(3,4,4-trifluoro-3-butenylthio)-1,3,4-thiadiazole,
2-(1,1,3,3-tetramethylbutylthio)-5-(3,4,4-trifluoro-3-butenylthio)-1,3,4-thiadiazole,
2,5-di(3,4,4-trifluoro-3-butenylthio)-1,3,4-thiadiazole,
2-cyclopropylmethylthio-5-(3,4,4-trifluoro-3-butenylthio)-1,3,4-thiadiazole,
3-chloro-5-(3,4,4-trifluoro-3-butenylthio)-1,2,4-thiadiazole;
3-chloro-5-(3,4,4-trifluoro-3-butenylthio)-1,2,4-oxadiazole;
2-(4-chlorophenylthio)-5-(3,4,4-trifluoro-3-butenylthio)-1,3,4-thiadiazole;
2-(4-chlorophenyl)-5-(3,4,4-trifluoro-3-butenyl-thio)-1,3,4-oxadiazole,
3,5-di(3,4,4-trifluoro-3-butenylthio)-1,2,4-thiadiazole,
3-(4-nitrophenylmethylthio)-5-(3,4,4-trifluoro-3-butenylthio)-1,2,4-thiadiazole,
2-(2-fluoroethylthio)-5-(3,4,4-trifluoro-3-butenylthio)-1,3,4-thiadiazole,
2-(2-cyanoethylthio)-5-(3,4,4-trifluoro-3-butenylthio)-1,3,4-thiadiazole,
2-propylthio-5-(3,4,4-trifluoro-3-butenylthio)-1,3,4-thiadiazole,
2-(1-methylethylthio)-5-(3,4,4-trifluoro-3-butenylthio)-1,3,4-thiadiazole,
2-(2-propenylthio)-5-(3,4,4-trifluoro-3-butenylthio)-1,3,4-thiadiazole,
2-phenylmethylthio-5-(3,4,4-trifluoro-3-butenylthio)-1,3,4-thiadiazole,
2-(4-bromophenylmethylthio)-5-(3,4,4-trifluoro-3-butenylthio)-1,3,4-thiadiazole,
2-(2-fluorophenylmethylthio)-5-(3,4,4-trifluoro-3-butenylthio)-1,3,4-thiadiazole,
2-(4-nitrophenylmethylthio)-5-(3,4,4-trifluoro-3-butenylthio)-1,3,4-thiadiazole,
2-(2-thienylmethylthio)-5-(3,4,4-trifluoro-3-butenylthio)-1,3,4-thiadiazole, 2-(4-chlorophenyl)-5-(3,4,4-trifluoro-3-butenylthio)-1,3,4-thiadiazole,
3-(4-fluorophenylmethyl)-5-(3,4,4-trifluoro-3-butenylthio)-1,2,4-oxadiazole,
3-(4-chlorophenyl)-5-(3,4,4-trifluoro-3-butenylthio)-1,2,4-oxadiazole,
3-(4-nitrophenyl)-5-(3,4,4-trifluoro-3-butenylthio-1,2,4-oxadiazole,
2-propyl-5-(3,4,4-trifluoro-3-butenylthio)-1,3,4-oxadiazole,
2-phenylmethyl-5-(3,4,4-trifluoro-3-butenylthio)-1,3,4-oxadiazole,
2-(4-chlorophenylmethyl)-5-(3,4,4-trifluoro-3-butenylthio)-1,3,4-oxadiazole,
2-(2-fluorophenylmethyl)-5-(3,4,4-trifluoro-3-butenylthio)-1,3,4-oxadiazole,
2-(4-fluorophenylmethyl)-5-(3,4,4-trifluoro-3-butenylthio)-1,3,4-oxadiazole,
2-(2,4-difluorophenylmethyl)-5-(3,4,4-trifluoro-3-butenylthio)-1,3,4-oxadiazole,
2-(2-phenylethyl)-5-(3,4,4-trifluoro-3-butenylthio)-1,3,4-oxadiazole,
2-(3-chlorophenyl)-5-(3,4,4-trifluoro-3-butenylthio)-1,3,4-oxadiazole,
2-(4-bromophenyl)-5-(3,4,4-trifluoro-3-butenylthio)-1,3,4-oxadiazole and
2-(4-fluorophenyl)-5-(3,4,4-trifluoro-3-butenylthio)-1,3,4-oxadiazole.

8. Compounds of the formula of claim 1 wherein X is oxygen.

9. Compounds of claim 8 selected from (3,4,4-trifluoro-3-butenyl) pentafluoropropionate mono diethyl etherate,
(3,4,4-trifluoro-3-butenyl) heptafluorobutyrate,
(3,4,4-trifluoro-3-butenyl) 4-chlorobenzoate,
(3,4,4-trifluoro-3-butenyl) 2-thiophenecarboxylate,
(3,4,4-trifluoro-3-butenyl) 5-nitro-2-furancarboxylate,
(3,4,4-trifluoro-3-butenyl) 2-pyrrolecarboxylate and
(3,4,4-trifluoro-3-butenyl) acetate.

10. Compounds of the formula of claim 1 wherein X is nitrogen.

11. Compounds of claim 10 selected from (3,4,4-trifluoro-3-butenyl) isothiocyanate,
N-(3,4,4-trifluoro-3-butenyl)succinimide and
N-(3,4,4-trifluoro-3-butenyl)saccharine.

12. A method of controlling nematodes which comprises applying to the locus where control is desired a nematicidally effective amount of a compound of claim 1.

13. A method of controlling nematodes which comprises applying to the locus where control is desired a nematicidally effective amount of a compound of claim 2.

14. A method of controlling nematodes which comprises applying to the locus where control is desired a nematicidally effective amount of a compound of claim 3.

15. A method of controlling nematodes which comprises applying to the locus where control is desired a nematicidally effective amount of a compound of claim 5.

16. A method of controlling nematodes which comprises applying to the locus where control is desired a nematicidally effective amount of a compound of claim 6.

17. A method of controlling nematodes which comprises applying to the locus where control is desired a nematicidally effective amount of at least one compound of claim 7.

18. A method of controlling nematodes which comprises applying to the locus where control is desired a nematicidally effective amount of a compound of claim 8.

19. A method of controlling nematodes which comprises applying to the locus where control is desired a nematicidally effective amount of a compound of claim 9.

20. A method of controlling nematodes which comprises applying to the locus where control is desired a nematicidally effective amount of a compound of claim 10.

21. A method of controlling nematodes which comprises applying to the locus where control is desired a nematicidally effective amount of a compound of claim 11.

22. A nematicidal composition comprising a nematicidally effective amount of a compound of claim 1 in an agriculturally acceptable carrier.

23. A nematicidal composition comprising a nematicidally effective amount of a compound of claim 2 in an agriculturally acceptable carrier.

24. A nematicidal composition comprising a nematicidally effective amount of a compound of claim 3 in an agriculturally acceptable carrier.

25. A nematicidal composition comprising a nematicidally effective amount of a compound of claim 5 in an agriculturally acceptable carrier.

26. A nematicidal composition comprising a nematicidally effective amount of a compound of claim 6 in an agriculturally acceptable carrier.

27. A nematicidal composition comprising a nematicidally effective amount of at least one compound of claim 7 in an agriculturally acceptable carrier.

28. A nematicidal composition comprising a nematicidally effective amount of a compound of claim 8 in an agriculturally acceptable carrier.

29. A nematicidal composition comprising a nematicidally effective amount of a compound of claim 9 in an agriculturally acceptable carrier.

30. A nematicidal composition comprising a nematicidally effective amount of a compound of claim 10 in an agriculturally acceptable carrier.

31. A nematicidal composition comprising a nematicidally effective amount of a compound of claim 11 in an agriculturally acceptable carrier.

32. A method of controlling helminths that infect animals, which comprises administering to an animal an anthelmintic amount of a compound of claim 1.

33. A method of controlling helminths that infect animals, which comprises administering to an animal an anthelmintic amount of a compound of claim 2.

34. A method of controlling helminths that infect animals, which comprises administering to an animal an anthelmintic amount of a compound of claim 3.

35. A method of controlling helminths that infect animals, which comprises administering to an animal an anthelmintic amount of a compound of claim 5.

36. A method of controlling helminths that infect animals, which comprises administering to an animal an anthelmintic amount of a compound of claim 6.

37. A method of controlling helminths that infect animals, which comprises administering to an animal an anthelmintic amount of a compound of claim 7.

38. A method of controlling helminths that infect animals, which comprises administering to an animal an anthelmintic amount of a compound of claim 9.

39. A method of controlling helminths that infect animals, which comprises administering to an animal an anthelmintic amount of a compound of claim 10 selected from N-(3,4,4-trifluoro-3-butenyl)succinimide and N-(3,4,4-trifluoro-3-butenyl)saccharine.

40. An anthelmintic composition comprising an effective amount of a compound of claim 1 in combination with a pharmaceutically acceptable carrier.

41. An anthelmintic composition comprising an effective amount of a compound of claim 2 in combination with a pharmaceutically acceptable carrier.

42. An anthelmintic composition comprising an effective amount of a compound of claim 3 in combination with a pharmaceutically acceptable carrier.

43. An anthelmintic composition comprising an effective amount of a compound of claim 5 in combination with a pharmaceutically acceptable carrier.

44. An anthelmintic composition comprising an effective amount of a compound of claim 6 in combination with a pharmaceutically acceptable carrier.

45. An anthelmintic composition comprising an effective amount of a compound of claim 7 in combination with a pharmaceutically acceptable carrier.

46. Compounds of the formula of claim 1 wherein $R^3$ is phenyl substituted by from one to five substituents, which may be the same or different.

47. The compounds of claim 46 wherein the phenyl substituents are selected from the group consisting of halo, trifluoromethyl, nitro, cyano, methylthio, methylsulfinyl, methylsulfoxy, methyl, isopropyl, t-butyl, methoxy, ethoxy, trifluoromethoxy, tetrafluoroethoxy, dimethylamino, phenoxy and phenyl.

48. The compounds of claim 5 wherein $R^4$ is phenyl substituted by from one to five substituents, which may be the same or different.

49. The compounds of claim 48 wherein the phenyl substituents are selected from the group consisting of halo, trifluoromethyl, nitro, cyano, methylthio, methylsulfinyl, methylsulfoxy, methyl, isopropyl, t-butyl, methoxy, ethoxy, trifluoromethoxy, tetrafluoroethoxy, dimethylamino, phenoxy and phenyl.

50. The compounds of claim 6 wherein $R^5$ is phenyl substituted by from one to five substituents, which may be the same or different.

51. The compounds of claim 50 wherein the phenyl substituents are selected from the group consisting of halo, trifluoromethyl, nitro, cyano, methylthio, methylsulfinyl, methylsulfoxy, methyl, isopropyl, t-butyl, methoxy, ethoxy, trifluoromethoxy, tetrafluoroethoxy, dimethylamino, phenoxy and phenyl.

52. A method of controlling nematodes which comprises applying to the locus where control is desired a nematicidally effective amount of the compound of claim 46 or 47.

53. A nematicidal composition comprising a nematicidally effective amount of a compound of claim 46 or 47 in an agriculturally acceptable carrier.

54. A method of controlling helminths that infect animals, which comprises administering to an animal an anthelmintic amount of a compound of claim 46 or 47.

55. An anthelmintic composition comprising an effective amount of the compound of claim 46 or 47 in combination with a pharmaceutically acceptable carrier.

56. A method of controlling nematodes which comprises applying to the locus where control is desired a nematicidally effective amount of the compound of claim 48 or 49.

57. A nematicidal composition comprising a nematicidally effective amount of a compound of claim 48 or 49 in an agriculturally acceptable carrier.

58. A method of controlling helminths that infect animals, which comprises administering to an animal an anthelmintic amount of a compound of claim 48 or 49.

59. An anthelmintic composition comprising an effective amount of the compound of claim 48 or 49 in combination with a pharmaceutically acceptable carrier.

60. A method of controlling nematodes which comprises applying to the locus where control is desired a nematicidally effective amount of the compound of claim 50 or 51.

61. A nematicidal composition comprising a nematicidally effective amount of a compound of claim 50 or 51 in an agriculturally acceptable carrier.

62. A method of controlling helminths that infect animals, which comprises administering to an animal an anthelmintic amount of a compound of claim 50 or 51.

63. An anthelmintic composition comprising an effective amount of the compound of claim 50 or 51 in combination with a pharmaceutically acceptable carrier.

* * * * *